(12) United States Patent
Otani et al.

(10) Patent No.: US 9,773,641 B2
(45) Date of Patent: Sep. 26, 2017

(54) METHOD AND APPARATUS FOR OBSERVING DEFECTS

(75) Inventors: Yuko Otani, Tokyo (JP); Yuta Urano, Yokohama (JP); Toshifumi Honda, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 287 days.

(21) Appl. No.: 13/993,838

(22) PCT Filed: Nov. 10, 2011

(86) PCT No.: PCT/JP2011/076011
§ 371 (c)(1),
(2), (4) Date: Jun. 13, 2013

(87) PCT Pub. No.: WO2012/081341
PCT Pub. Date: Jun. 21, 2012

(65) Prior Publication Data
US 2013/0277553 A1    Oct. 24, 2013

(30) Foreign Application Priority Data
Dec. 16, 2010  (JP) ................. 2010-280512

(51) Int. Cl.
*G01N 21/00*    (2006.01)
*H01J 37/26*    (2006.01)
(Continued)

(52) U.S. Cl.
CPC ........ *H01J 37/261* (2013.01); *G01N 21/8806* (2013.01); *G01N 21/9501* (2013.01)

(58) Field of Classification Search
None
See application file for complete search history.

(56) References Cited

U.S. PATENT DOCUMENTS

| 6,407,373 B1 * | 6/2002 | Dotan ............... G01N 21/9501 250/201.3 |
| 2005/0122508 A1 * | 6/2005 | Uto ..................... G01N 21/956 356/237.2 |

(Continued)

FOREIGN PATENT DOCUMENTS

| JP | 7-270144 | 10/1995 |
| JP | 7-325041 | 12/1995 |

(Continued)

OTHER PUBLICATIONS

Office Action in JP 2010-280512, dated Mar. 6, 2014, (1 page, in Japanese); [partial English language translation].

*Primary Examiner* — Andrew Smyth
(74) *Attorney, Agent, or Firm* — Baker Botts L.L.P.

(57) ABSTRACT

Disclosed are a method and an apparatus for observing defects by using an SEM, wherein, in order to observe defects on a wafer at high speed and high sensitivity, positional information of defects on a sample, which has been optically inspected and detected by other inspecting apparatus, and information of the conditions of the optical inspection having been performed by other inspecting apparatus are obtained, and optically detecting the defects on the sample placed on a table, on the basis of the thus obtained information, and on the basis of the detected positional information of the defect on the sample placed on the table, the positional information of the defect having been inspected and detected by other inspecting apparatus is corrected, then, the defects on the sample placed on the table are observed by the SEM using the thus corrected positional information of the defects.

16 Claims, 12 Drawing Sheets

(51) Int. Cl.
    *G01N 21/88*    (2006.01)
    *G01N 21/95*    (2006.01)

(56) References Cited

U.S. PATENT DOCUMENTS

| | | | |
|---|---|---|---|
| 2007/0057184 A1* | 3/2007 | Uto | G01N 21/95607 250/310 |
| 2008/0073524 A1* | 3/2008 | Nishiyama | G01N 23/225 250/307 |
| 2010/0019150 A1* | 1/2010 | Nishiyama | G01N 23/225 250/310 |

FOREIGN PATENT DOCUMENTS

| | | | | |
|---|---|---|---|---|
| JP | 11-125602 | 5/1999 | | |
| JP | 2000-352697 | 12/2000 | | |
| JP | 2001/133417 | 5/2001 | | |
| JP | 2001-133417 | 5/2001 | | |
| JP | 2001133417 A | * 5/2001 | ......... | G01N 21/9501 |
| JP | 2005/156537 | 6/2005 | | |
| JP | 2005-156537 | 6/2005 | | |
| JP | 2006-261162 | 9/2006 | | |
| JP | 2007-71803 | 3/2007 | | |
| JP | 2007-235023 | 9/2007 | | |
| JP | 20070/235023 | 9/2007 | | |

* cited by examiner

METHOD AND APPARATUS FOR OBSERVING DEFECTS

BACKGROUND

The present invention relates to a method for observing defects and its apparatus having a function of detecting defects and the like existing on a sample surface, or sample surface or around the sample surface.

For example, in a semiconductor device manufacturing process, when a pattern defect (hereinbelow, described as a defect but it includes on foreign material and a pattern defect) such as foreign material, a short circuit or wire break exists on a semiconductor substrate (wafer), it becomes the failure factor of insulation failure, short circuit and the like. Further, in accordance with microminiaturization of circuit pattern formed on a wafer, finer defects may be the cause of capacitor insulation failure, breakage of gate oxide film or the like. Among these defects, the foreign material may be caused in various statuses, e.g., caused from a movable part of a transfer device, caused from a human body, react-generated with process gas inside a processing device, or may be mixed in chemicals and materials. Further, the pattern defect such as short circuit or wire break is caused due to variation of process conditions, variation of the processing device or the like. Accordingly, it is important for mass-production of semiconductor device to detect defects caused in the manufacturing process, quickly find the source of outbreaks of the defects and stop manufacture of defective products.

Conventionally, as a method of thorough inquiry into the factor of occurrence of defects, there has been a method of first specifying a defect position with a defect inspecting apparatus, then observing and classifying the defects in detail with a SEM (Scanning Electron Microscope) or the like, and performing a comparison with a database, to estimate the factor of occurrence of the defects.

Note that the defect inspecting apparatus is an optical defect inspecting apparatus to irradiate the surface of a semiconductor substrate with laser, and perform dark field observation on scattered light from a defect, to specify the position of the defect, an optical appearance inspecting apparatus to irradiate with a lamp or laser, or an electron beam, to detect a bright field optical image of the semiconductor substrate, and by comparing this with reference information, specify a defect position on the semiconductor substrate, or a SEM inspecting apparatus. Regarding such observing method, there is disclosure in Japanese Published Unexamined Patent Application No. Hei 7-270144 (Patent Literature 1) and or Japanese Published Unexamined Patent Application No. 2000-352697 (Patent Literature 2).

Further, regarding an apparatus to observe a defect with a SEM, U.S. Pat. No. 6,407,373 (Patent Literature 3), Japanese Published Unexamined Patent Application No. 2007-71803 (Patent Literature 4) and Japanese Published Unexamined Patent Application No. 2007-235023 (Patent Literature 5) respectively disclose a method and its apparatus for detecting a position on a sample with an optical microscope attached to a SEM defect inspecting apparatus using positional information defect on the sample detected with the other inspecting apparatus, correcting the defect positional information obtained by detection with other inspecting apparatus, and observing (reviewing) the defect in detail with the SEM defect inspecting apparatus, and, upon observation of defect with a SEM defect inspecting apparatus, optically detecting the height of the sample surface and adjusting the sample surface to a focus position of the SEM.

SUMMARY

In recent LSI manufacturing, by microminiaturization of circuit pattern in correspondence with needs for high integration, the width of wiring pattern formed on a wafer is reduced. On the other hand, to ensure wiring electric conductivity, the height of the wiring pattern is high.

In correspondence with this, in the optical defect inspecting apparatus, microminiaturization of the size of defect to be detected is needed.

In such situation, detecting a defect with an optical defect inspecting apparatus or an optical appearance inspecting apparatus, and based on the coordinates of the detected defect, observing the defect with a SEM is performed.

When a defect on the surface of the semiconductor substrate is detected by using the optical defect inspecting apparatus, to raise the throughput in the old apparatus or the throughput of inspection, in some cases, the surface of a semiconductor substrate is scan-irradiated with a laser beam for dark field illumination of the surface of semiconductor substrate having a large spot size. In this case, the accuracy of positional coordinates obtained from the position of the laser beam spot scanning the surface of the semiconductor substrate includes a large error component.

When detailed observation is performed on a defect using a SEM based on the positional information of the defect including such large error component, in some cases, a defect to be observed is not included in the field of view of a SEM for observation at far higher magnification than that of an optical defect inspecting apparatus. In this case, to include the defect image to be observed in the field of view of the SEM, a search for the defect is conducted while it is being moved in the field of view of the SEM. It takes time for this purpose, and it becomes the factor of degradation of the throughput of the SEM observation. Accordingly, to include the defect detected with the optical defect inspecting apparatus or the optical appearance inspecting apparatus in the field of view of the SEM, there is a SEM defect observing apparatus, having an optical microscope, to detect a defect detected with an optical defect inspecting apparatus or an optical appearance inspecting apparatus with high coordinate accuracy in the defect observing apparatus and to infallibly include the defect in the observing field of view of the SEM, in a SEM defect inspecting apparatus.

To observe a minute defect with the SEM defect observing apparatus, the optical microscope for defect detection incorporated in the defect observing apparatus is also required to detect minute defects.

To detect weak light from a minute defect, high sensitivity by arrangement of a filter having a function of selecting and controlling scattering direction to be detected polarized light and transmittance, on a detection optical path, and defect observation under plural optical conditions with varied illumination condition and detection condition, are promoted. However, as the detection sensitivity of a defect differs in accordance with illumination wavelength, illumination direction, defect shape and defect direction, it is necessary to perform defect detection and observation under optical conditions which differ in accordance with defect shape or defect direction. Accordingly, as the optical conditions to be set are increased, it takes time for setting appropriate optical conditions, to lower the throughput.

Accordingly, one of the objects of the present invention is to provide a defect observing method and its apparatus using an apparatus having an optical microscope capable of detecting various defects on a wafer at a high speed and at high sensitivity.

Further, some defect shape has illumination azimuth angle dependency in scattered light intensity distribution. At some illumination azimuth angle, it is impossible to obtain strong scattered light in a region detectable with the optical microscope incorporated in the defect observing apparatus, and it is impossible to actualize the defect.

Accordingly, one of the objects of the present invention is to provide a defect observing method and its apparatus using an apparatus having an optical microscope capable of detecting various defects on a wafer and defects in different defect directions at a high sensitivity.

To solve the above-described problem, in the present invention, provided is a defect observing method comprising: obtaining positional information of a defect on a sample detected by optical inspection with another inspecting apparatus, information on conditions of the optical inspection with said other inspecting apparatus, and information on the result of inspection; placing the sample on a table to observe the defect detected with the other inspecting apparatus with a SEM; setting detection conditions to optically detect the defect on the sample placed on the table based on the obtained information on the conditions of the optical inspection with the other inspecting apparatus and information on the result of inspection; detecting the defect on the sample placed on the table based on the set optical detection condition and obtaining the positional information of the defect on the table; correcting the positional information of the defect detected by inspection with the other inspecting apparatus based on the obtained positional information of the defect on the table; and observing the defect on the sample placed on the table with the SEM using the corrected positional information of the defect.

Further, to solve the above-described problem, in the present invention, provided is a defect observing method comprising the steps of: obtaining positional information of a defect on a sample detected by optical inspection with another inspecting apparatus, information on conditions of the optical inspection with said other inspecting apparatus, and information on the result of inspection; placing the sample on a table to observe the defect detected with the other inspecting apparatus with a SEM; setting detection conditions to optically detect the defect on the sample placed on the table based on the obtained information on the conditions of the optical inspection with the other inspecting apparatus and information on the result of inspection; detecting the defect extracted from the defects on the sample placed on the table based on the set optical detection condition, and obtaining the positional information of the extracted defect on the table; correcting the positional information of the defect detected by inspection with the other inspecting apparatus based on the obtained positional information of the extracted defect on the table; an observing the defect on the sample placed on the table with the SEM using the corrected positional information of the defect.

Further, to solve the above-described problem, in the present invention, provided is a defect observing apparatus comprising: table means movable while holding a sample; SEM means for observing the sample placed on the table means; optical microscope means for detecting a defect on the sample placed on the table means; defect information storage means for storing positional information of the defect on the sample detected by optical inspection with another inspecting apparatus, information on the optical inspection with the other inspecting apparatus, and inspection result information; and control means for controlling the table, the SEM and the optical microscope, wherein the control means sets optical inspection conditions detected by optically inspecting the defect on the sample with the other inspecting apparatus stored in the defect information storage means and detection condition to detect the detected defect with the optical microscope means based on the inspection result information, detects the defect detected with the other inspecting apparatus on the sample placed on the table means using the optical microscope means under the set detection condition by controlling the optical microscope means, and obtains the positional information of the defect on the table means, corrects the positional information of the defect detected with the other inspecting apparatus stored in the defect information storage means based on the obtained positional information of the defect on the table means, and controls the table means based on the corrected positional information, performs image sensing on the defect detected with the other inspecting apparatus using the SEM means, and obtains the defect image.

According to the present invention, when a defect detected with an optical defect detecting apparatus is observed in detail with a SEM or the like, it is possible to include the defect as the object of reservation in the observation field of view of the SEM or the like infallibly and at a high speed and increase the throughput of detailed defect inspection using the SEM or the like. Further, it is possible to detect various defects on a substrate at a high speed and high sensitivity.

Further, it is possible to improve the accuracy of classification and shape determination of detected defects, and the defect detection sensibility.

DESCRIPTION OF THE PREFERRED EMBODIMENTS

Figure 1A:
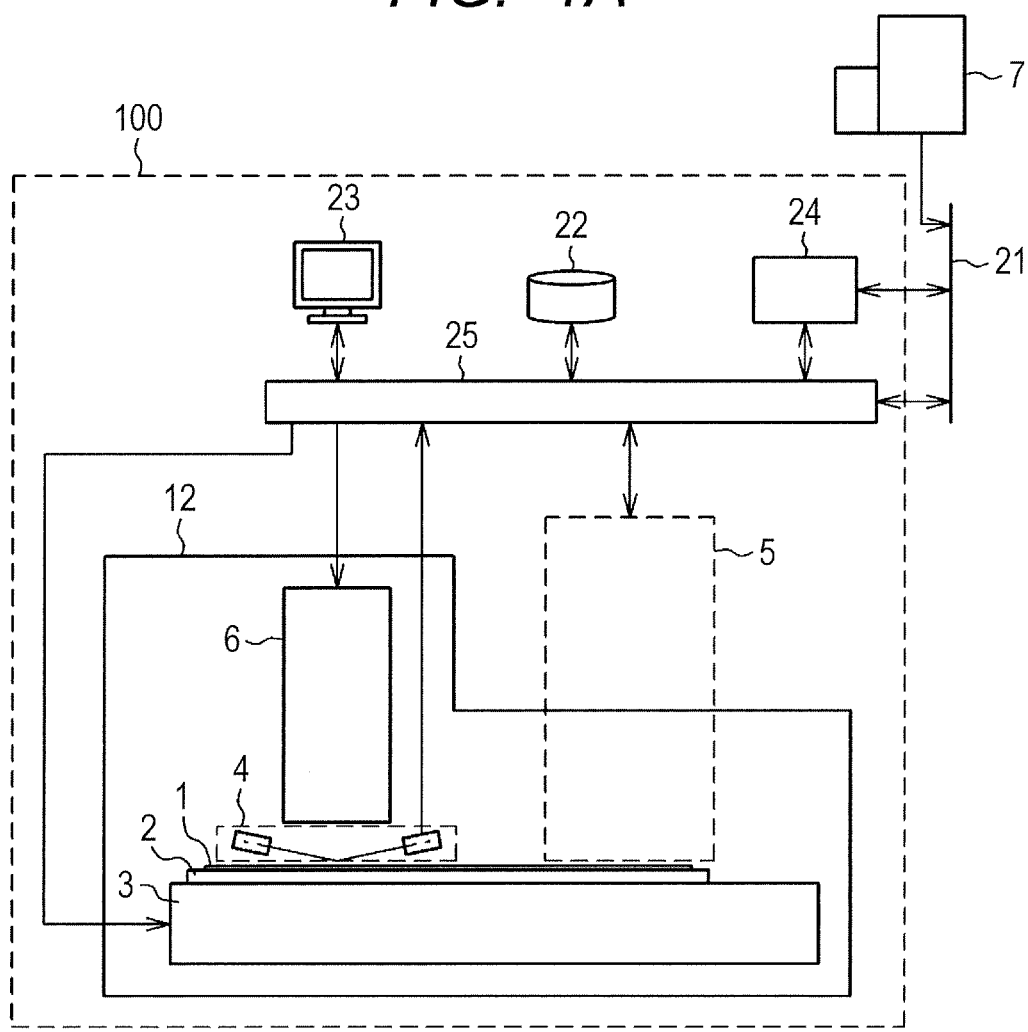
FIG. 1A is a block diagram showing the schematic structure of a defect observation apparatus in an embodiment of the present invention.

Hereinbelow, an embodiment of the present invention will be described in detail appropriately using the drawings. FIG. 1A shows an example of the structure of a defect observing apparatus 100 according to the present invention. The defect observing apparatus 100 according to the present embodiment has a sample 1 as a subject of inspection, a sample holder 2 to hold this sample, a stage 3 capable of moving this sample holder 2 to move the entire surface of the sample 1 to a position under a scanning electron microscope 6 (hereinbelow described as SEM), the SEM 6 to conduct detailed observation on the sample 1, an optical height detecting system 4 to adjust the focal point of the SEM 6 to the surface of the sample 1, an optical microscope 5 to optically detect a defect on the sample 1 and obtain detailed positional information of the defect on the sample 1, a vacuum vessel 12 to contain the SEM 6 and an objective lens 505 (shown in FIG. 2) of the optical microscope 5, a control system 25 to control the SEM 6 and the optical height detecting system 4 and the optical microscope 5, a user interface 23, a database 22, a network 21 for connection to a higher system such as an optical defect inspecting apparatus 7 (the other defect inspecting apparatus 7), and a storage device 24 to hold external data or the like from the other defect inspecting apparatus 7 obtained via this network 21 and provide it to the control system 25.

Further, in the defect observing apparatus 100, the stage 3, the optical height detecting system 4, the SEM 6, the user interface 23, the database 22, the storage device 24 and the optical microscope 5 are connected to the control system 25, and the control system 25 is connected via the network 21 to the higher system (for example, the other defect inspecting apparatus 7).

Figure 1B:
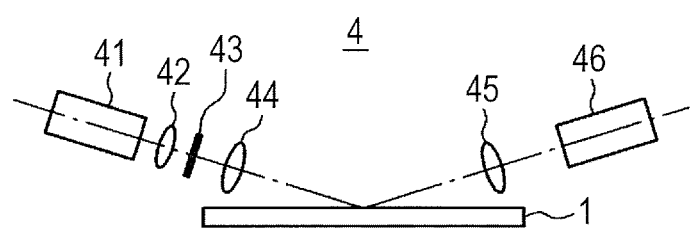
FIG. 1B is a side view showing the schematic structure of an optical height detecting system of the defect observing apparatus in the embodiment of the present invention.

As shown in FIG. 1B, the optical height detecting system 4 has a light source 41 to emit height measuring light, a condenser lens 42 to collect the height measuring light emitted from the light source, a slit 43 to be irradiated with light collected with the condenser lens, an imaging lens 44 to form an image of light transmitted through the slit as the height measuring light (slit image) on the surface of the sample 1, a condenser lens 45 to collect the height measuring light reflected from the sample 1, and a detector 46 to detect the height measuring light collected with the condenser lens and convert it into an electric signal. The information on the height measuring light converted into the electric signal with the detector is sent to the control system 25, and the height is calculated.

Hereinbelow, the details of the respective parts will be described using FIGS. 2 to 5.

Figure 2A:
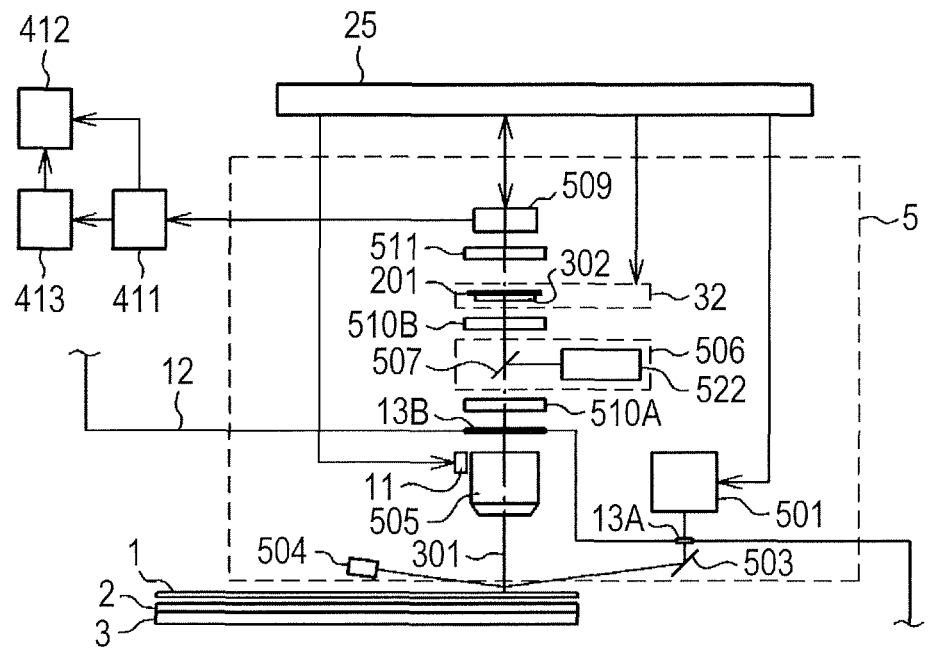
FIG. 2A is a block diagram showing the schematic structure of an optical microscope of the defect observing apparatus in the embodiment of the present invention.

FIG. 2A shows an example of the optical microscope 5 shown in the present embodiment.

The optical microscope 5 in FIG. 2A has a dark field illumination unit 501 capable of emitting light having one or plural wavelengths, a mirror 503 to irradiate the surface of the sample 1 with illumination light emitted from the dark field illumination unit 501, the objective lens 505 to collect or conduct bright field observation on the scattered light from the sample 1, a height control mechanism 11 to control the height of the objective lens, a bright field illumination light source 506 to conduct bright field observation on the sample 1 and a half mirror 507 to emit the light from the bright field illumination light source 506 on the sample, lenses 510A and 510B to extract a pupil plane 302 of the objective lens 505, an imaging lens 511 to form an image of the sample 1, a spatial distribution optical element 201 to be inserted in the pupil plane 302 of the objective lens extracted with the lenses 510A and 510B, a beam trap 504 to collect reflected light which is caused by a light emitted from the dark field illumination unit 501 to the sample 1 and directly reflected from the sample 1, an optical element selecting mechanism 31 (see FIG. 9) to select an optical element of the spatial distribution optical element 201, a solid-state image sensing device 509 for imaging the image of the sample 1 formed with the imaging lens 511, an image processing unit 411 to process the image obtained with the solid-state image sensing device 509, an image display unit 412 to display the image obtained with the solid-state image sensing device 509, and an image storage unit 413 to store the image obtained with the solid-state image sensing device 509. The position where the solid-state image sensing device 509 is installed may be a conjugate position with respect to the sample surface or may be in the vicinity of the respective conjugate positions.

Further, to transmit the light emitted from the dark field illumination unit 501 of the optical microscope 5 and the light scattered from the surface and near the surface of the sample 1 to outside the vacuum vessel 12, the vacuum vessel 12 has vacuum sealing windows 13A and 13B.

Further, the dark field illumination unit 501 (shown in FIG. 4) of the optical microscope 5 and the spatial distribution optical element 201 of the optical microscope 5, the spatial distribution optical element holder 32 and the solid-state image sensing device 509 of the optical microscope 5 are connected to the control system 25, and controlled so as to work in correspondence with the optical conditions set with the control system 25. Further, the height control mechanism 11 is connected to the control system 25, and the solid-state image sensing device 509 is connected to the image processing unit 411.

The lenses 510A and 510B are employed to form the pupil plane 302 of the objective lens 505 inside a space formed by the lens 510, the imaging lens 511 and the spatial distribution optical element 201, and by driving the spatial distribution optical element holder 32, one of the spatial distribution optical element 201 selected from the one or plural spatial distribution optical elements 201 held with the spatial distribution optical element holder 32 is placed on the pupil plane 302 formed inside the lens 510, the imaging lens 511, and the spatial distribution optical element 201.

In the present embodiment, the lenses 510A and 510B and the imaging lens 511, as one set, form the image of the sample 1 on a detection surface of the solid-state image sensing device 509. In the present embodiment, two lenses 510, the imaging lens 511 and the spatial distribution optical element 201 are used, however, the number of the lenses 510 may be one or more than two.

In the defect observing apparatus 100 having the above structure, especially the optical microscope 5 has a function of re-detecting (hereinbelow, described as detecting) the position of the defect on the sample 1 which has been detected with the other inspecting apparatus 7, by using the positional information of the defect detected with the other defect inspecting apparatus 7, and a function of setting the dark field illumination unit 501, the spatial distribution optical element 201 and the spatial distribution optical element holder 32 or setting any one of them by using the information on the defect (for example, luminance, the size of luminescent spot, scattering direction, polarized light) detected with the other defect inspecting apparatus 7. The height control mechanism 11 and the optical height detecting system 4 have a function as focusing means for performing sample focusing. The control system 25 has a function as position information correcting means for correcting the positional information of the defect based on the defect positional information detected with the optical microscope 5. The SEM 6 has a function of observing the defect, the positional information of which has been corrected with the control system 25. The stage 3, holding the sample 1, moves between the optical microscope 5 and the SEM 6 such that the defect detected with the optical microscope 5 can be observed with the SEM 6.

Next, the optical microscope 5' having a function of variably controlling the direction of illumination will be described using FIG. 2B.

By using the optical microscope 5' having a function of variably controlling the direction of illumination, it is possible to suppress the influence of defect direction on detection sensitivity.

Figure 2B:
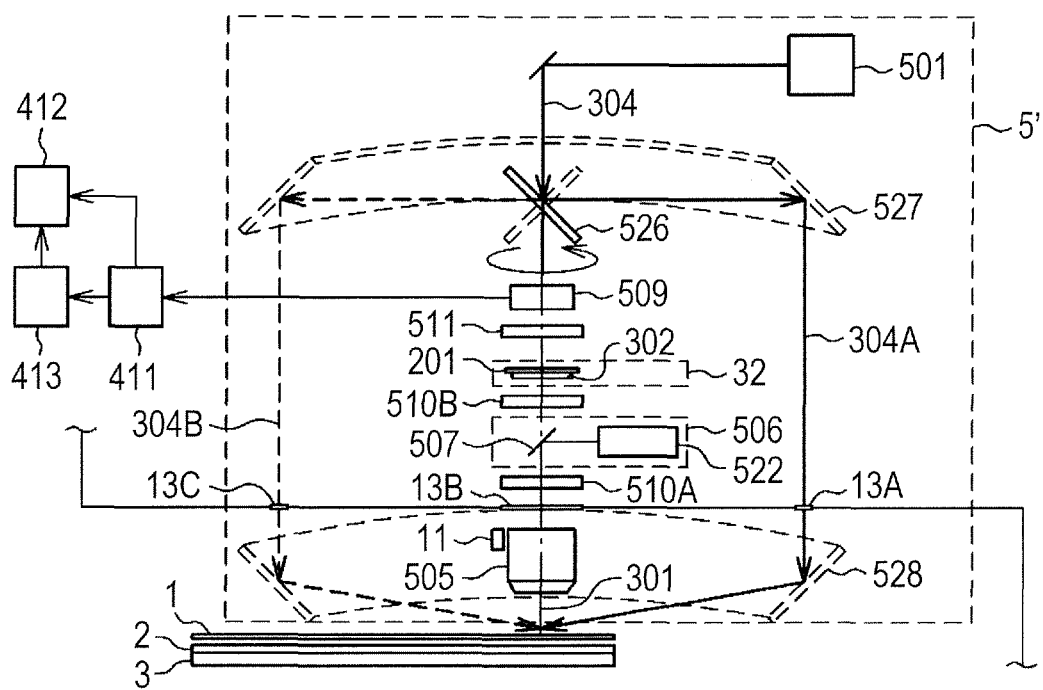
FIG. 2B is a block diagram showing the schematic view of the optical microscope having another structure in the embodiment of the present invention.

In the structure of the optical microscope 5' shown in FIG. 2B, the elements the same as the elements of the optical microscope 5 described in FIG. 2A have the same numerals. The difference from the structure of the optical microscope 5 described in FIG. 2A is the arrangement of the dark field illumination unit 501 and the illumination method for the sample 1. In the structure shown in FIG. 2B, to perform dark field illumination on the sample 1 with selection from plural azimuth directions using the dark field illumination unit 501, the illumination light from the dark field illumination unit 501 is introduced from a position above the optical microscope 5', then the optical path is selected to 304A or 304B using a swing mirror 526, then reflected with a conic epi illumination mirror 527 and transmitted through the vacuum sealing window 13A or 13C, thus led inside the vacuum vessel 12, and reflected by a conical mirror 528 inside the vacuum vessel 12, to obliquely illuminate the sample 1.

In the optical microscope 5' shown in FIG. 2B, the swing mirror 526 has a function of rotating about an optical axis 301 of a detection optical system formed with the objective lens 505, the lenses 510A and 510B, the imaging lens 511 and the solid-state image sensing device 509, as the rotation axial center. The conic epi illumination mirror 527 reflects the illumination light 304 reflected from the swing mirror downward. The illumination light 304 reflected from the conic epi illumination mirror 527 is reflected by the conical mirror 528 and incident on the sample 1. The conic epi illumination mirror 527 and the conical mirror 528 may have an annular conical shape to reflect light in a region from azimuth angle $-\pi$ to $\pi$, with an angle within a plane as 0, about the optical axis 301 of the detection optical system as the axial center, or may have a shape in which a part of the annular conical shape is omitted. For example, it may be a half cut shape to reflect only the region of $\pi$ from azimuth angle 0 with some angle as 0. In the case of half cut shape, to trap light reflected with the sample 1, the region from $-\pi$ to 0 may be a beam trap. When the swing mirror 526 stays at the position indicated by the solid line, the illumination light 304 passes through the optical path 304A in the figure. On the other hand, when the swing mirror 526 stays at the position indicated with the dotted line, the illumination light 304 passes through the optical path 304B in the figure, thus it is possible to illuminate the sample 1 at the azimuth angle different from the illumination light 304A.

The light scattered from the sample 1 by the irradiation of the illumination light 304A or 304B is transmitted through the objective lens 505, the lens 510, the imaging lens 511 and the spatial distribution optical element 201, and is image-formed. The solid-state image sensing device 509 arranged on the image forming plane performs image sensing on the thus formed optical image. The azimuth angle of the swing mirror 526 is controlled with the control system 25 (FIG. 1). Further, the detection signal obtained by the rotation azimuth angle of the swing mirror 526 and the solid-state image sensing device 509 can be stored in the storage device 24 (FIG. 1). Further, to trap the zero-order light (regular reflection light) reflected from the sample 1, a beam trap may be provided on the rear surface of the reflecting surface of the swing mirror 526 to reflect the illumination light 304.

Further, the swing mirror 526, having the function of rotating about the optical axis 301 of the detection optical system as the rotation axial center, and the function of variably controlling the inclination of the reflecting surface of the swing mirror 526 with respect to the optical axis 301 of the detection optical system, and conic epi illumination mirror 527 and conical mirror 528, in which the reflecting surface of the conic epi illumination mirror 527 and the reflecting surface of the conical mirror 528 are aspherical shapes, may be used. It is possible for the optical microscope 5 to illuminate the sample 1 at different azimuth angles and incident angles by changing the rotation azimuth angle of the swing mirror 526 and the inclination of the reflecting surface of the swing mirror 526 with respect to the optical axis 301 of the detection optical system. For example, it may be arranged such that when the reflecting surface of the conic epi illumination mirror 527 has an ellipsoidal shape and the conical mirror 528 has a parabolic surface shape, one focal point of the ellipsoidal shape of the conical incident-light mirror 527 and one focal point of the parabolic surface of the conical mirror 528 are the same point.

The rotation azimuth angle of the swing mirror 526 and the inclination of the reflecting surface of the swing mirror 526 with respect to the optical axis 301 of the detection optical system are controlled with the control system 25 (FIG. 1). Further, the information on the rotation azimuth angle of the swing mirror 526 and the inclination of the reflecting surface of the swing mirror 526 with respect to the optical axis 301 of the detection optical system can be stored, together with the detection signal obtained by image sensing with the solid-state image sensing device 509 on the optical image, in the storage device 24 (FIG. 1). The conic epi illumination mirror 527 and the conical mirror 528 may have an annular conical shape to reflect light in a region from azimuth angle $-\pi$ to $\pi$, with an angle within a plane as 0, about the optical axis 301 of the detection optical system as the axial center, or may have a shape in which a part of the annular conical shape is omitted. For example, it may be a half cut shape to reflect only the region of $\pi$ from azimuth angle 0 with some angle as 0. Further, the aspherical shapes of the conic epi illumination mirror 527 and the conical mirror 528 may not be an ellipsoidal shape and a parabolic surface.

Figure 3A:
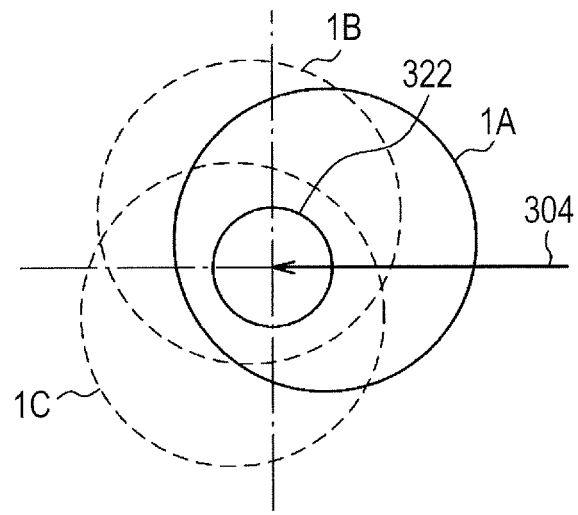
FIG. 3A is a plane view of a stage showing illumination region on the stage having a rotating function.
Figure 3B:
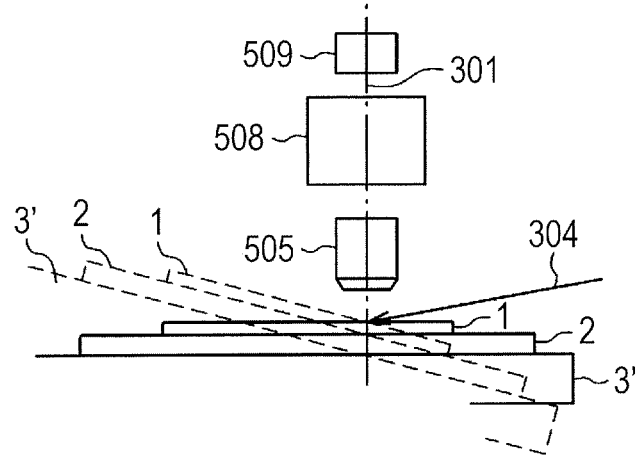
FIG. 3B is a front view of the stage having rotating and tilt functions showing a status where the stage is tilted.

Next, a method of changing the illumination direction with respect to the sample 1 without use of the swing mirror 526 described in FIG. 2B will be described using FIGS. 3A and B. FIG. 3A is a diagram explaining the optical microscope using a stage having a rotation and tilt functions as a stage 3'. To suppress the variation of sensitivity due to difference of inclination 303 (see FIG. 6) of defect with respect to the illumination light 304, the illumination direction is fixed. But, by using the stage 3' with rotation and tilt functions, it is possible to rotate the sample 1 about a measurement region 322 of the optical microscope 5 and irradiate the defect from illumination direction different from 1A, 1B and 1C. FIG. 3B is a schematic diagram of the optical microscope capable of irradiating a defect at different incident angles by using the stage 3' having a function of tilting the sample 1.

As shown in FIGS. 3A and 3B, by using the optical microscope 5 with the stage 3' having a function of rotating or rotating and tilting the sample 1, it is possible to variably control the illumination light to the defect even though the incident direction of the illumination light 304 is fixed.

In the present embodiment, the bright field illumination unit 522 described in FIGS. 2A and B has a bright field light source 506 and the half mirror 507 used for irradiating the sample 1 with light radiated from the bright field light source 506 along the optical axis 301 of the detection optical system. The ratio between the reflection and transmission of the half mirror 507 may be arbitrary. Note that when the light intensity of the bright field light source 506 is sufficiently ensured, a structure to lead more scattered light from a defect to the lenses 510A and B, the imaging lens 511, the spatial distribution optical element 201 and the solid-state image sensing device 509 will be more preferable.

As the bright field light source 506, a lamp, or laser will be used. When laser is used, by changing the half mirror 507 with a dichroic mirror, it is possible to brighten the illumination and lead more scattered light to the solid-state image sensing device 509. Otherwise, it may be arranged such that a mechanism (not shown) to, upon dark field observation, remove the half mirror 507 from the optical axis 31 of the detection optical system is provided. In such case, it is possible to lead more scattered light to the solid-state image sensing device 509.

Figure 4A:
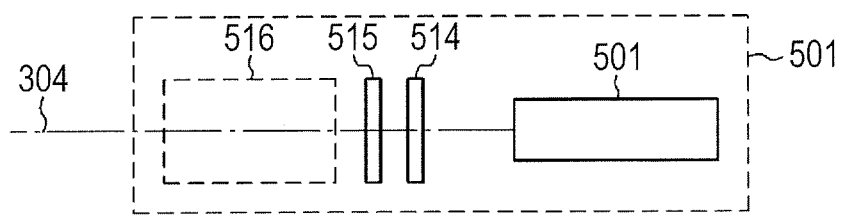
FIG. 4A is a diagram showing an illumination optical system used in the embodiment of the present invention, and is a plane view of the illumination optical system having a structure provided with an illumination light source and an optical filter, a wave plate, and a lens group.
Figure 4B:
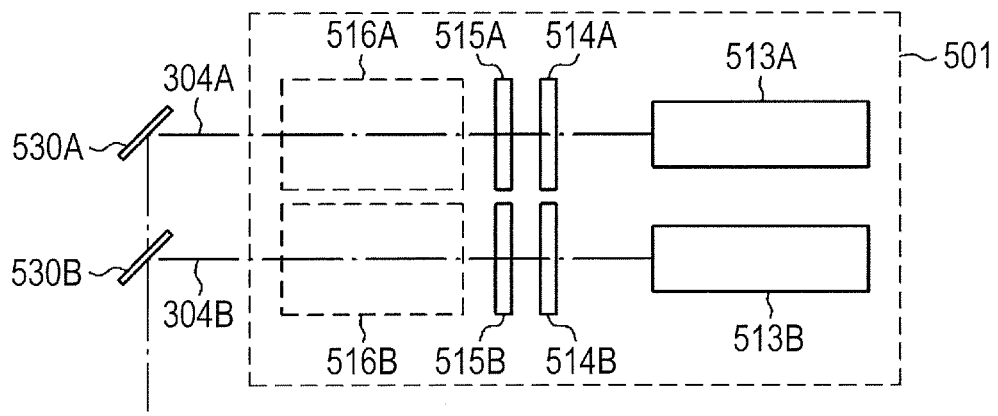
FIG. 4B is a diagram showing the illumination optical system used in the embodiment of the present invention, and is a plane view of the illumination optical system having a structure provided with two systems having the illumination light source and the optical filter, the wave plate and the lens group.
Figure 4C:
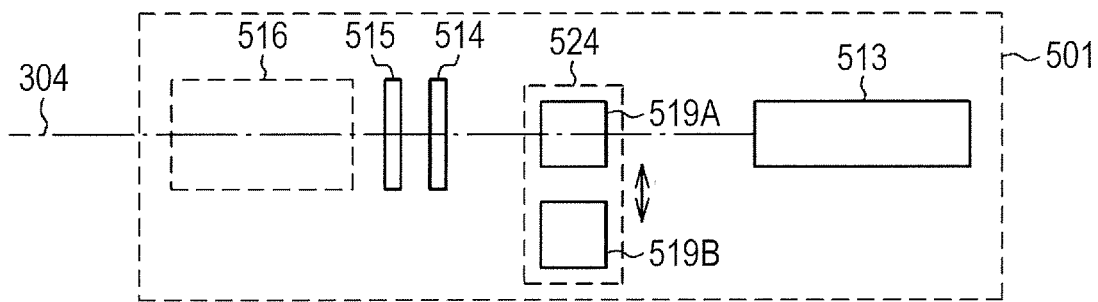
FIG. 4C is a diagram showing the illumination optical system used in the embodiment of the present invention, and is a plane view of the illumination optical system having a structure provided with non-linear optical part for wavelength conversion.

FIGS. 4A to 4C show an example of the structure of the dark field illumination unit 501 described in FIGS. 2A and 2B. The dark field illumination unit 501 shown in FIG. 4A has, for example, an illumination light source 513 to emit visible light laser, ultraviolet laser, vacuum ultraviolet laser, a lamp or a light emitting diode, an optical filter 514 to control the intensity of illumination light, a wave plate 515 to control the polarization direction of the illumination light, and a lens group 516 to narrow the illumination light to the sample 1.

When an attenuator, an ND filter or a polarizer is used as the optical filter 514 in FIG. 4A, it is possible to parallel-translate or rotate-move the optical filter, or exchange it with another optical filter, or remove the optical filter so as to control to an appropriate illumination light amount in accordance with defect size or the like. Further, the wave plate 515 is capable of change the illumination polarization, and it can be changed or taken in and out arbitrarily.

The illumination light source 513 is a laser oscillator, a broad band white lamp or a light-emitting diode. The laser oscillator oscillates, for example, visible light (400 nm-800 nm) having a wavelength of 405 nm, 455 nm, 488 nm or 532 nm, or ultraviolet light having a wavelength 400 nm or lower, or vacuum-ultraviolet light having a wavelength 200 nm or lower, and any one of continuous oscillation laser and pulse oscillation laser can be used. As a method of selection from them, when the continuous oscillation laser is used, a low-price and stable, and small sized apparatus can be realized. The wavelength of the illumination light source 513 is not limited to the above-described wavelengths, but laser capable of multi-wavelength oscillation may be used. To detect a defect on the sample surface or near the surface, a light source to irradiate the surface of the sample 1 with short-wavelength ultraviolet laser, vacuum ultraviolet laser or a visible short-wavelength blue laser is preferable. To detect a defect inside the sample or crystal defect, a light source to irradiate the surface of the sample 1 with visible laser or infrared laser is preferable.

When sensitivity to detect a defect on the surface of the sample 1 or near the surface of the sample 1 is required, ultraviolet light is used. In such case, the objective lens 505, the vacuum sealing window 13B, the half mirror 507, the lens 510, the imaging lens 511 and the spatial distribution optical element 201 are formed of optical elements of quartz or the like for a ultraviolet region corresponding element, or reflective optical elements. When further sensitivity is required, vacuum ultraviolet light is used. In such case, the objective lens 505, the vacuum sealing window 13B, the half mirror 507, the lens 510, the imaging lens 511 and the spatial distribution optical element 201 are formed of optical elements of fused quartz or the like for a vacuum ultraviolet region corresponding element, or reflective optical elements. Further, the entire optical path in the optical microscope 5 is provided in a vacuum environment or, for example, in nitrogen gas atmosphere, to prevent absorption of the vacuum ultraviolet rays in propagating inside the vacuum. As the propagation of the vacuum ultraviolet is the object, the filled gaseous body is not limited to nitrogen.

When the sample 1 is a mirror surface sample, P-polarized laser light is used for irradiation of the sample 1. When the surface of the sample 1 is covered with a metal thin film, S-polarized laser light is used. The P-polarized light or S-polarized linear polarized light is used for more efficient observation of the scattered light and implementation of good S/N observation. That is, when the S-polarized light is used upon observation of the mirror surface sample, the scattering performance is degraded and the absolute scattered light amount is reduced, thus the efficiency is degraded, accordingly, P-polarized illumination is appropriate. On the other hand, when the P-polarized light illumination is performed upon observation of a metal thin film or the like, the scattered light from the substrate is intensified, and minute defect or minute foreign material cannot be observed, accordingly, S-polarized illumination is appropriate.

The dark field illumination unit 501 in FIG. 4B has two illumination light sources 513A and 513B for illumination with two lights having mutually different wavelengths, optical filters 514A and 514B provided on respective optical paths so as to control respective illumination intensities of illumination light 304A and 304B emitted from the illumination light source having mutually different wavelengths, wave plates 515A and 515B provided on respective optical paths 701A and 701B so as to control the respective polarization direction of the two illumination lights 304A and 304B, and lens groups 516A and 516B provided on the respective optical paths of the illumination lights 304A, 304B provided on the respective optical paths to narrow the respective two illumination lights 304A and 304B to the sample 1. It is capable of simultaneously irradiating the surface of the sample 1 with the illumination light having mutually different two wavelengths.

The dark field illumination unit 501 in FIG. 4C can convert the illumination light 304 into different wavelengths by, taking in and out nonlinear optical crystals 519A and 519B on the optical path of the illumination light source 513 using a nonlinear optical crystal selecting mechanism 524 for wavelength conversion of the illumination light 304 emitted from the illumination light source 513 for illumination with mutually different two wavelengths, and can irradiate the surface of the sample 1 with mutually different two wavelengths. It may be arranged such that the surface of the sample 1 is irradiated with short-wavelength illumination light 304, by using long wavelength laser as the illumination light source 513, and converting it to a double harmonic wave, triple harmonic wave, quadruple harmonic wave or the like using a nonlinear optical crystal 519.

Figure 5A:
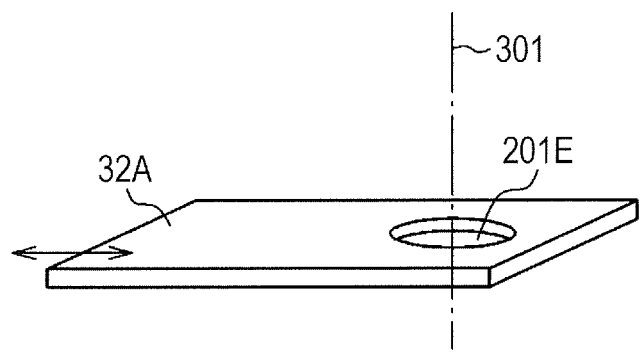
FIG. 5A is a perspective view showing the schematic structure of a spatial distribution optical element holder used in the embodiment of the present invention.
Figure 5B:
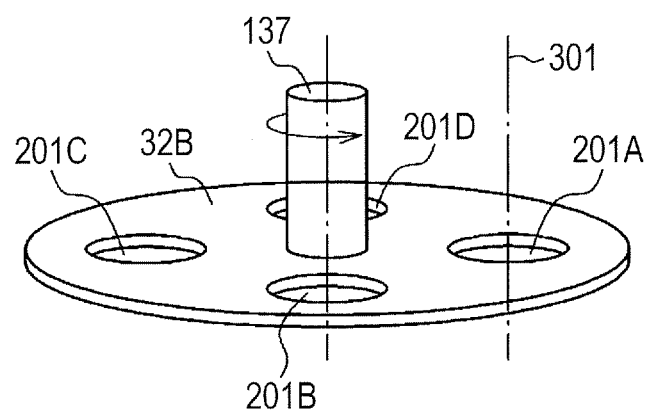
FIG. 5B is a perspective view showing the schematic structure of the spatial distribution optical element holder having plural optical elements used in the embodiment of the present invention.

FIGS. 5A and 5B show an example of the spatial distribution optical element holder 32. In the present embodiment, it may be arranged such that as the spatial distribution optical element 201, plural spatial distribution optical elements 201 having different properties are held with the spatial distribution optical element holder 32, (in the example shown in FIG. 5A, the spatial distribution optical element holder 32A shows presence/absence of the spatial distribution optical element 201, and in the example shown in FIG. 5B, the spatial distribution optical element holder 32B shows four types of spatial distribution optical elements 201A to 201D), and any one of the spatial distribution optical elements 201A to 201D is selected an inserted into the pupil plane 302 of the objective lens 505. Further, the spatial distribution optical elements 201A to 201D may not be provided on the optical axis 301 of the detection optical system.

As shown in FIG. 5A, as the spatial distribution optical element holder 32A is slid in the arrow direction, it has a function of taking in and out the spatial distribution optical element 201 inserted in the pupil plane 302 of the objective lens 505 on the optical axis 381 of the detection optical system, to select presence/absence of the spatial distribution optical element 201. In the spatial distribution optical element holder 32A in FIG. 5A, the spatial distribution optical element 201 is one, however, plural spatial distribution optical elements 201 may be provided.

The spatial distribution optical element holder 32B in FIG. 5B shows a mechanism to select the spatial distribution optical elements 201A to 202D inserted in the pupil plane 302 on the optical axis 301 of the objective lens 505 on the lens 510, the imaging lens 511, and the spatial distribution optical element 201. The selecting mechanism has the spatial distribution optical element holder 32B to arrange plural distribution polarizing elements 201A to 201D having different properties, and a rotary driver 137 to axially rotate the spatial distribution optical element holder 32B. The spatial distribution optical element holder 32B is a mechanism to select any one of the plural spatial distribution optical elements 201A to 201D in correspondence with type of minute defect to be detected.

Upon bright field observation or when the spatial distribution optical element is not used, to avoid disturbance of obtained image, the spatial distribution optical element holder 32 shown in FIGS. 5A and 5B is placed to a position where the spatial distribution optical element 201 is not set and then observation is carried out, otherwise, changed to the place where a parallel glass plate having a thickness equivalent to the spatial distribution optical element 201 is set in the spatial distribution optical element holder 32. The parallel glass plate having the thickness equivalent to the spatial distribution optical element 201 is set so as to avoid change of the optical path length upon removal of the spatial distribution optical element 201 to disturb formation of the image of the sample 1 on the solid-state image sensing device 509. Otherwise, a mechanism not to set the parallel glass plate but control the position of the imaging lens 511 to form the image or the solid-state image sensing device 509, to form an image on the solid-state image sensing device 509 may be used.

Next, the spatial distribution optical element 201 attached to the spatial distribution optical element holder 32 will be described. The spatial distribution optical element 201 is an optical element capable of increasing the ratio of scattered light from the foreign material with respect to the scattered light from the substrate surface and performing high S/N in defect detection. The spatial distribution optical element 201 has any one or combination of a spatial filter, a phase shifter, an optical filter (ND filter), a color filter, a wave plate, a polarizing plate, a liquid crystal, a magneto-optical modulator and a photonic crystal, and has a function of transmitting and polarization direction controlling scattered light on optical conditions (wavelength, transmittance, polarization, phase difference) such that the ratio of the scattered light from the substrate surface to the scattered light from the foreign material is high.

The method for determining the arrangement of the phase shifter, the inclination of the phase delay axis and the inclination of the phase advancing axis of the wave plate, the rotary direction with a polarization direction control device, a light shielding region in the spatial filter, the transmittance polarization direction of the polarizer, the transmittance of dimming filter, voltage applied to the liquid crystal device, voltage applied to the magneto-optical modulator, the optical property of photonic crystal and the like, which form the spatial distribution optical element 201, are determined based on the scattered light intensity distribution obtained by scattered light simulation or actual measurement.

Any one or both of the spatial distribution optical element 201 and the spatial distribution optical element holder 32 are connected to the control system 25 to select or control the optical conditions.

The scattered light simulation is irradiating the sample 1 with laser as the illumination light 312 from a diagonally above position, regarding the light scattered with a minute foreign material or minute defect placed on the sample 1, calculating the intensity distribution and polarizing distribution of the scattered light in the surface closest to the sample 1 (pupil plane 302) in the optical element of the detection optical system closest to the sample 1.

Figure 6:
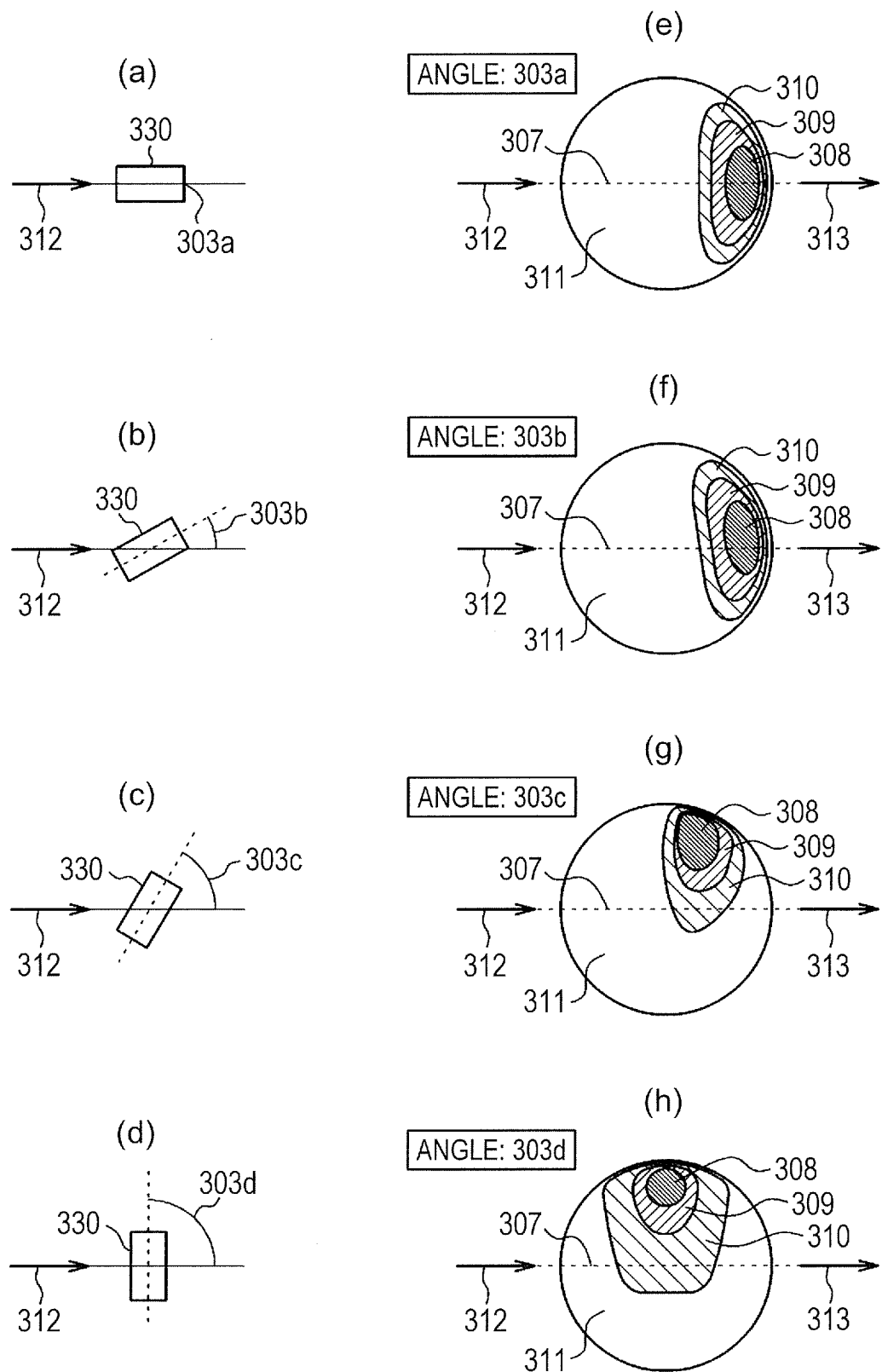
FIG. 6 is a diagram showing a defect calculation model example by incident angle and a scattered light intensity distribution example, obtained by using scattered light simulation.

FIG. 6 shows an example of scattered light intensity distribution of anisotropic defect obtained by scattered light simulation. As shown in FIG. 6, in accordance with defect type, the scattered light intensity distribution and the polarizing distribution differ by the defect inclination 303 with respect to the illumination light. Accordingly, even in the defect has the same size, the sensitivity varies in accordance with the defect inclination 303 with respect to incident light. Otherwise, detection cannot be performed in accordance with defect inclination 303 with respect to incident light. Accordingly, as in the case of the optical microscope 5' shown in FIG. 2B or as shown in FIG. 3A or B, the illumination with variable control of direction is effective to perform stable defect detection.

FIGS. 6(a) to (d) show an example of defect calculation model of scattered light simulation. It is an example of calculation model to obtain the scattered light intensity distribution when the inclination 303 of some defect 330 is changed to (a) 303a, (b) 303b, (c) 303c and (d) 303d with respect to illumination incident direction. Further, FIGS. 6(e) to (h) show an example of scattered light intensity distribution of defect by the illumination incident angle. These distributions are obtained by scattered light simulation. Note that the obtained scattered light intensity distribution is not limited to these examples but may be described as a polarizing component. The polarizing component may be radial polarizing, azimuth polarizing, linear polarization inclined in the range of $\pi$ to $-\pi$, polarized light angle, or elliptic (circular) polarizing. The respective scattered light intensity distributions are the results of scattered light simulations in the left FIGS. 6 (a) to (d) calculation models.

FIGS. 6 (e) to (h) show scattered light intensity distribution fSB (r, θ) when the defect is inclined to angles (e) 303a, (f) 303b, (g) 303c and (h) 303d with respect to the illumination light incident angle. Further, an axis 307 in the respective scattered light intensity distribution indicates an axis to adjust the incident surface of illumination on the pupil plane 302. An arrow 312 indicates the incident direction of illumination light, and an arrow 313 indicates regular reflection direction of the illumination light. In the respective polarized light intensity distributions in FIGS. 6 (e) to (h), a region 308 is a region in which the scattered light intensity is high, a region 309 is a region in which the scattered light intensity is rather high, and a region 310 is a region in which the scattered light intensity is rather low, and a region 311 is a region in which the scattered light intensity is low. They indicate relative relation of intensity in the same distribution, and even in the same region in the respective distributions, the intensities are not necessarily the same (for example, the region 308 in the scattered light intensity distribution figure at the angle 303a in FIG. 6(e) and the region 308 in the scattered light intensity distribution figure at the angle 303b in FIG. 6(e) do not necessarily indicate the same intensity).

According to the scattered light intensity distributions shown in FIGS. 6(e) to (h), it is understood that when there is no inclination of the defect with respect to the illumination incident angle or the inclination is very small, the scattered light from the defect is strongly scattered frontward, and in accordance with increase in the inclination of the defect with respect to the illumination incident angle, the strong scattering region is moved to the side. Further, there is a tendency of increase of upper scattered light component.

In this manner, even in the same defect, the intensity distribution of scattered light differs due to difference of inclination of the defect with respect to illumination incident angle. Accordingly, it is possible to increase the ratio of the scattered light from the substrate surface with respect to the scattered light from the foreign material and perform high S/N defect detection by changing the illumination incident direction or rotating the sample 1, or appropriately setting and providing the polarizing filter, or combining them. Note that the defect of which the scattered light intensity distribution is obtained is not limited to these defects, but it may have a defect shape such as a spherical defect, a polished defect, stacking fall or scratch, in-film foreign material, and a crystal-caused defect. Further, not only the scattered light intensity distribution but intensity distribution by polarizing of respective defects and intensity distribution by polarizing component of scattered light from the respective defects may be used. The obtained polarized light is not limited to these light but may be linear polarized light in which the polarizing angle is inclined from $\pi$ to $-\pi$, or elliptic (circular) polarized light.

As an example has been shown in FIG. 6, in the optical property of the scattered light, the scattered light intensity distribution and the polarization distribution differ in accordance with defect type, shape and direction. Accordingly, it is necessary for high sensitivity detection to select illumination condition and detection condition corresponding to defect shape and defect direction. For example, as the illumination conditions, illumination wavelength, illumination incident azimuth angle and elevation angle, intensity and the like, and as the detection conditions, detection wavelength, detection polarization, sensor sensitivity, detection scattering angle and the like, are conceivable.

Further, it is possible to suppress the scattered light from the sample 1 or amplify scattered light from line defect by changing light oscillation direction, i.e., polarization direction. Accordingly, by appropriately setting and providing a rotary polarizer on the pupil plane 302 of the optical microscope 5 shown in FIG. 2A or around the pupil plane 302 of the optical microscope 5' shown in FIG. 2B, it is possible to increase the ratio of the scattered light from the substrate surface with respect to the scattered light from the foreign material and to perform high S/N defect detection.

Next, an example of effect when liquid crystal is used as an element of the spatial distribution optical element 201 will be described. It is possible to precisely control polarization direction which is not realized with a ½ wave plate or ¼ wave plate using quartz crystal by controlling the voltage applied to the liquid crystal or controlling the direction of rubbing subjected to the orientation film. Further, it may be arranged such that plural polarization direction control devices are arranged two dimensionally and used as one spatial distribution optical element 201. At that time, it is possible for the plural polarization direction control devices forming the spatial distribution optical element 201 to control the rotary polarization angle, and it is possible to appropriately control the rotary polarization angle in correspondence with scattered light distribution.

Note that the liquid crystal is a crystal, in an intermediate state between liquid and crystal, having liquid fluidity and crystal anisotropic property of crystal. The liquid crystal includes liquid crystal having chirality with rotary property and liquid crystal having no chirality without rotary property.

In the case of liquid crystal having chirality, liquid crystal particles in contact with the substrate are rotated in a vertical direction and arrayed. The direction of the rotation is determined with the chirality of the liquid crystal. When light is transmitted through the liquid crystal, the light polarization direction is rotated in accordance with the array of the liquid crystal particles, to change the polarization status. When a voltage is applied using a power source to the liquid crystal having chirality, the horizontally arrayed liquid crystal particles arise vertically. As the liquid crystal particles arise, the rotary property is lost. It is possible to change the polarization direction by controlling the angle of arise of the liquid crystal particles with the level of the applied voltage.

Further, the spatial distribution optical element, in which rubbing is performed on the orientation film, the array of the liquid crystal particles in the liquid crystal is controlled by voltage application, and the polarization direction is controlled, will be described.

When there is no application voltage, the liquid crystal is arrayed along the rubbing direction of the orientation film, and the array of the liquid crystal particles in the liquid crystal is not rotated and parallel between the orientation film and an outermost layer. When a voltage is applied between electrodes, the liquid crystal particles around the electrode are rotated in the plane, however, as the liquid crystal particles around the orientation film are arrayed along the rubbing direction, the array of the liquid crystal particles is rotated in the liquid crystal. When light is transmitted through the liquid crystal in this status, the light polarization direction is rotated in accordance with the array of the liquid crystal particles, thus it is possible to change light polarization status. It is possible to change the polarization direction by controlling the rotary angle of the liquid crystal particles in a plane parallel to the orientation film in accordance with level of application voltage to the electrodes.

Next, an example of the effect when the polarization control device using magnet-optical effect is applied as an element of the spatial distribution optical element 201 will be described. An example of the spatial distribution optical element 201 in which the polarization direction control device using a transparent magnetic body utilizing magnet-optical effect is shown. In this example, by controlling the magnetization direction of the transparent magnetic body 222 held between two transparent substrates, the polarization direction is controlled using Faraday rotation.

Further, the magnetization direction is controlled by application of external magnetic field or by application of stress on the crystal with a piezoelectric actuator, or by application of electric field or by application of external magnetic field and by application of stress on the crystal with a piezoelectric actuator. Note that when the rotary property is not necessary upon bright field observation or the like, it is possible to easily eliminate the rotary property by not applying electric field, or not applying electric field, or not applying external magnetic field.

Figure 7A:
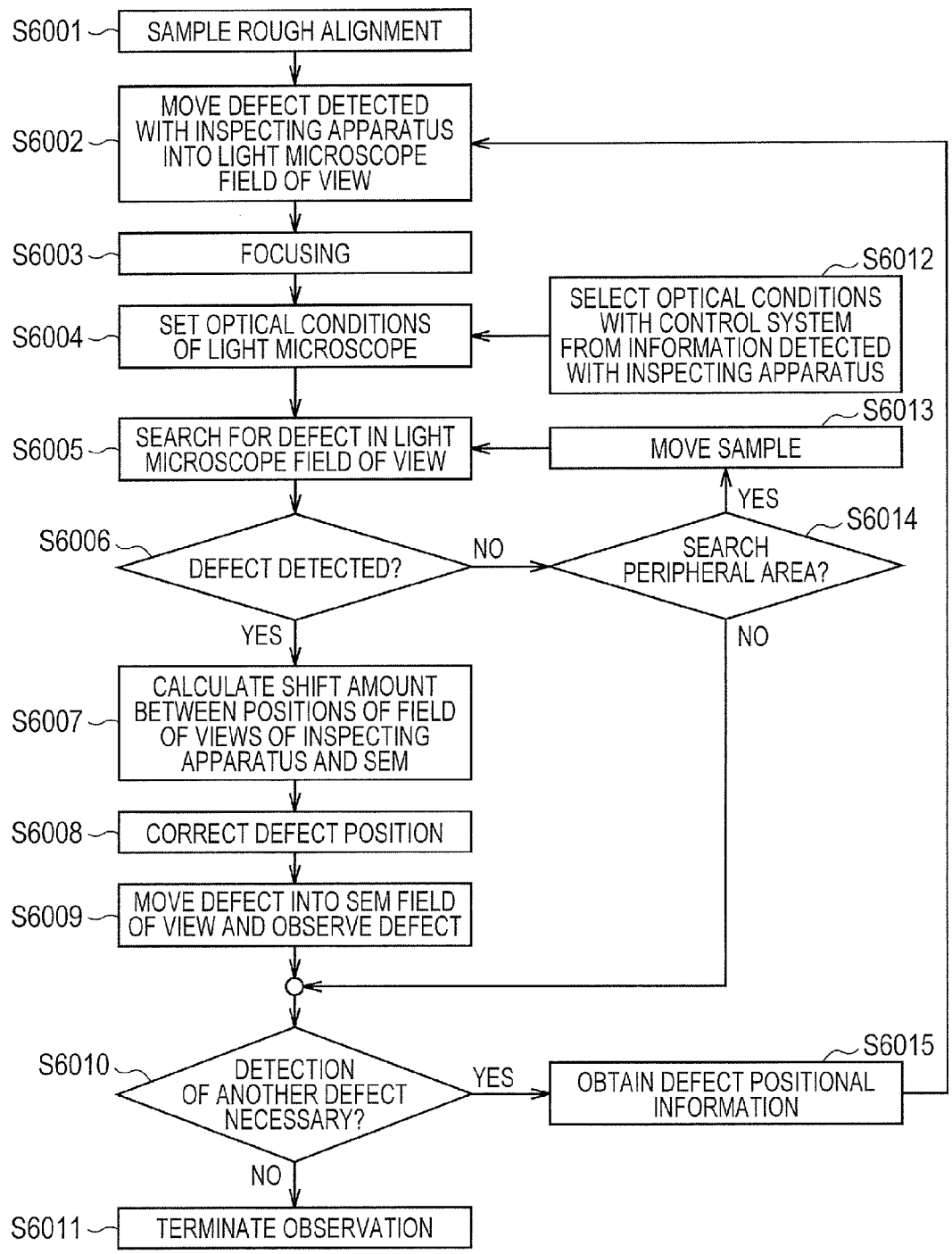
FIG. 7A is a flowchart showing a procedure of defect observation in the embodiment of the present invention.

Next, the flow of defect observation using the defect observing apparatus 100 will be described using FIG. 7A. First, the sample 1 is transferred via an unshown load lock chamber onto a sample holder 2 in the vacuum vessel 12. Then, the sample 1 is moved in the field of view of the optical microscope 5 or 5' under the control of the stage 3. At this time, there is a possibility that the sample 1 is shifted from the focus position of the optical microscope. When the height of the sample 1 is shifted from the focus position, the objective lens 505 and the mirror 503 are moved in the Z (height) direction so as to set the sample 1 to the focus position of the optical microscope 5 using the height control mechanism 11. A method of determining the moving amount in the Z direction will be described later.

To observe the defect on the sample 1 placed on the stage 3 of the defect observing apparatus 100 shown in FIG. 1, using the positional information of a defect on the sample 1, detected with another defect inspecting apparatus 7, wafer alignment to align the reference position of the sample 1 to the reference of the stage 3 is performed (step S6001). This wafer alignment is performed using a bright field observation image detected with the optical microscope 5 or 5' shown in FIG. 2A or B. Upon bright field detection, the illumination light is emitted from the bright field illumination light source 506, then reflected by the half mirror 507 provided on the optical axis 301 of the detection optical system and emitted to the sample 1 through the objective lens 505. The reflection light from the sample 1 is passed through the lens 510, the imaging lens 511 and the spatial distribution optical element 201, and image-formed with the solid-state image sensing device 509. Note that the bright field light source 506 is, for example, a lamp. In the bright field observation in the present embodiment, the spatial distribution optical element 201 inserted onto the optical axis 301 of the detection optical system is changed with a parallel glass plate having the same thickness. When alignment is performed on the outer shape of the sample 1 (when the sample 1 is a wafer, for example, orientation flat or notch), the positioning point of the sample 1 and a several number of images of the outer shape are obtained and processed.

Next, the stage 3 is moved to include the defect on the sample 1 to be observed in the field of view of the optical microscope 5 or 5', using the positional information of the defect previously detected with the other defect inspecting apparatus 7 and stored in the storage device 24 (step S6002). Next, the objective lens 505 is moved with the height control mechanism 11 to perform focusing (step S6003). Next, the optical conditions of the optical microscope 5 are set to the optical conditions set with the control system 25 (step S6004). The optical conditions are any of illumination conditions or detection conditions, or combination of illumination conditions and detection conditions. The illumination conditions include any of or a combination of illumination wavelength, illumination incident angle, illumination azimuth angle, illumination intensity, illumination polarization and the like. The detection conditions include sensitivity (gain) and storage time of the solid-state image sensing device 509, optical conditions (polarization, transmittance, wavelength, phase difference and the like) of the spatial distribution optical element 201, and the like.

The control system 25 performs selection of the optical conditions of the optical microscope 5 or 5' from the inspection information of the sample 1 outputted from the other inspecting apparatus (step S6012). The inspection information of the sample 1 outputted from the other defect inspecting apparatus 7 is inspection information having inspection results including any of or a combination of defect coordinates, a defect signal, a defect shape, polarization of defect scattered light, defect type, defect label, defect feature amount and a scattering signal on the surface of the sample 1, and inspection conditions including any of or a combination of illumination incident angle of the inspecting apparatus, illumination wavelength, illumination azimuth angle, illumination intensity, illumination polarization, the azimuth angle of the detector, the elevation angle of the detector, and the detection region of the detector. In case that plural sensors are installed to the other inspecting apparatus 7, the inspection information of the sample 1 outputted from each of the sensors or the inspection information of the sample 1 obtained by integrating plural sensor outputs is used.

Figure 7B:
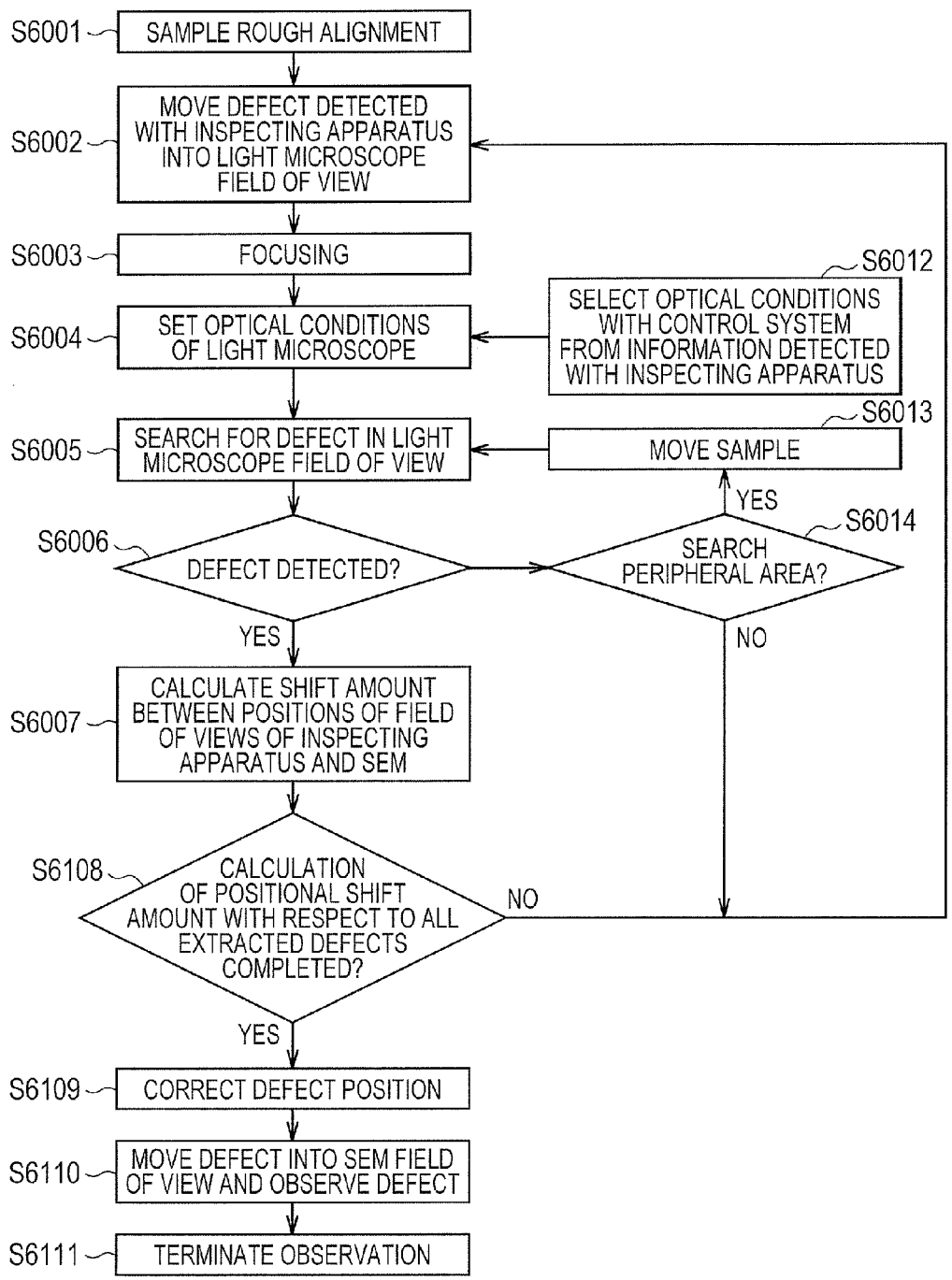
FIG. 7B is a flowchart showing the procedure of defect observation in the embodiment of the present invention, and showing processing when many defects to be observed exist.

The image processing unit 411 searches for a defect from the image obtained with the optical microscope 5 or 5' and the solid-state image sensing device 509 (step S6005). In case a defect is detected (step S6006—YES), a difference between the defect position detected by the optical microscope 5 or 5' and the defect positional information previously detected by the other defect inspecting apparatus 7 is calculated. And from the calculated difference and the defect positional information previously detected by the other defect inspecting apparatus 7, the shift amount of the field of view position of the SEM 6 with respect to the defect when observed with the SEM 6 is calculated (step S6007). Based on the calculated shift amount, the positional information of the defect previously detected by the other defect inspecting apparatus 7 is corrected (step S6008), then based on the corrected positional information, the stage 3 is moved. Then the defect with corrected positional information is moved into the field of view of the SEM 6, and the SEM 6 observes the defect (step S6009). At this time, the information on the observed defect is set to the control system 25, which performs processing such as display on the user interface 23, registration into the database 22, automatic defect classification and the like. In FIG. 7B, the processing from S6001 to S6007 is the same as that described in FIG. 7A.

FIG. 7B shows a processing flow when a large number of defects to be observed exist. When a large number of defects to be observed exist, several typical defects are extracted, then as in the case of the processing described in FIG. 7A, the processing from step S6001 to S6007 is sequentially repeatedly performed on these extracted defects. Regarding each of the extracted defects, from the difference between the positional information of the defect previously detected by the other defect inspecting apparatus 7 and the defect detection position with the optical microscope 5 or 5', using the positional information of the respective defects previously detected by the other defect inspecting apparatus 7, the shift amount of the field of view position of the SEM 6 with respect to the defect on the sample 1 when observed by the SEM 6 is calculated (step S6007). When the shift amount between the defect position detected by the other defect inspecting apparatus 7 and the field of view of the SEM has been obtained regarding all the extracted defects (YES at step S6108), next, at step S6109, using the information on the obtained shift amount, regarding defects other than the typical several defects, notch detected by the optical microscope 5 or 5', the positional information previously obtained by the other defect inspecting apparatus 7 is corrected. Next, at step S6110, based on the corrected positional information, the stage 3 is driven to move the defect into the field of view of the SEM 6, then the large number of defects to be observed are sequentially observed with the SEM 6. The information on the observed defect is sent to the control system 25, which performs processing such as display on the user interface 23, registration into the database 22, automatic defect classification and the like.

As described above, by setting the optical conditions corresponding to the defect with the optical microscope 5 or 5' then re-detecting the defect, which has been detected by the other defect inspecting apparatus 7, and correcting the positional information of the detect, it is possible to obtain more accurate positional information of the defect, detected by the other defect inspecting apparatus 7, on the defect observing apparatus 100. As a result, as it is possible to control the position of the stage 3 so as to infallibly include the defect detected by the other defect inspecting apparatus 7 in the field of view of the SEM, in comparison with the case where the optical conditions of the optical microscope of the conventional defect observing apparatus are fixed, it is possible to improve the throughput of the case where the defect observing apparatus 100 observes the defect.

Note that when the defect has not been detected in the above-described defect detection procedure (step S6006-NO), as it is conceivable that the defect is outside the field of view of the optical microscope 5, a search may be performed in the peripheral part of the field of view of the optical microscope 5. When a search is performed in the peripheral part (step S6014—YES), the sample 1 is moved by an amount corresponding to the field of view (step S6013), and the processing is performed from the above-described defect detection procedure (step S6005). Further, when the search of the peripheral part is not performed (step S6014-NO), the processing is proceeded in accordance with the procedure.

For example, based on the luminance information obtained with the other inspecting apparatus 7, as the optical filter 514 having an appropriate density is set to control the illumination intensity of the optical microscope 5 or 5', or when the dark field illumination light source 513 is illumination having variable illumination intensity, as the intensity of the illumination itself is controlled, it is possible to quickly set the illumination intensity correspondence with the size of the defect. Accordingly, it is possible to suppress ghost or degradation of coordinate accuracy which may occur in a huge defect, and it is possible not only to reduce the inspection time but also to improve defect detection rate and coordinate accuracy.

Further, when the other defect inspecting apparatus 7 has plural sensors and capable of collecting scattered light at different scattering angles, it is possible to estimate the direction and shape of the object defect from the difference of output by the sensors. Based on this estimation, by setting the optical conditions such as illumination wavelength, illumination incident angle, detection polarization and transmittance, it is possible to perform high sensitive defect detection.

Further, an example of defect observation procedure when the output data from the other defect inspecting apparatus 7 is used for setting the initial optical conditions of the optical microscope 5 or 5' will be described. When the defect detection has not been performed in the above-described defect detection procedure (step S6006-NO), as it is conceivable that the initial optical conditions of the optical microscope 5 or 5' set by the control system 25 are inappropriate, the optical conditions of the optical microscope 5 or 5' may be set again. When the optical conditions of the optical microscope 5 or 5' are set again, using the output data of the optical microscope 5 or 5' or the output data of the optical microscope 5 or 5' and the initial optical conditions, the optical conditions of the optical microscope 5 or 5' are selected again by the control system 25, then the optical conditions of the optical microscope 5 or 5' are set again, and the processing is performed from the above-described defect detection procedure.

In the defect observation procedure shown in FIG. 7, by performing the complicated setting of the optical conditions of the optical microscope 5 or 5' using the output data from the other inspecting apparatus, it is possible to enable high-speed defect observation.

Figure 8A:
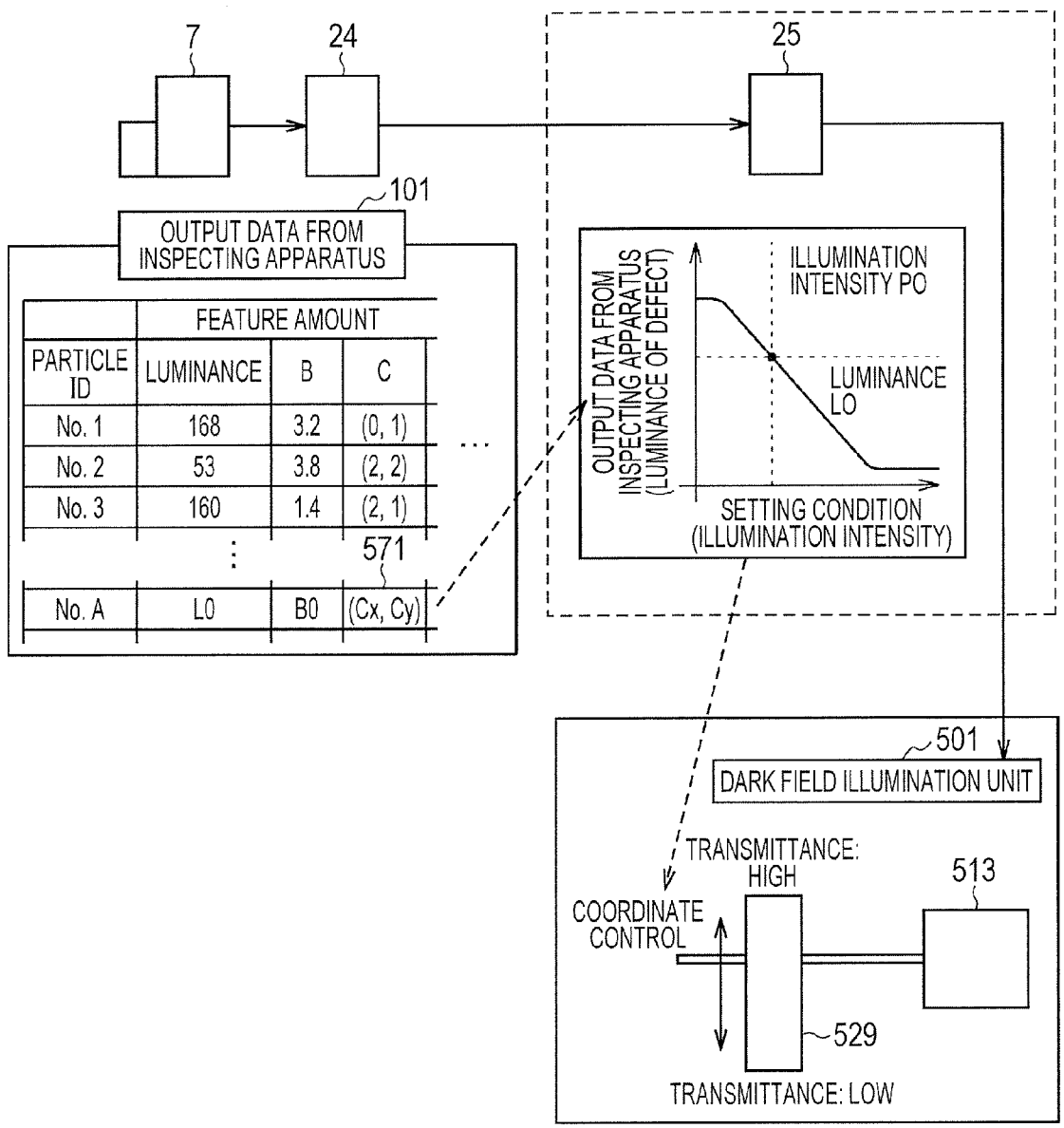
FIG. 8A is a block diagram showing the flow of data upon defect observation in the embodiment of the present invention.

An example of use of specific output information from the other defect inspecting apparatus 7 will be described using FIGS. 8A and B. FIG. 8A is an example where the illumination intensity in set in proportional to the luminance of the defect outputted from the inspecting apparatus. Output data 101 from the other defect inspecting apparatus 7 is stored in the storage device 24. In the processing system 25, luminance value L0 of a defect 571 to be detected in the above-described stored output data 101 of the other defect inspecting apparatus 7 is read, and based on the luminance value L0, illumination intensity P0 of the dark field illumination unit 501 is set. The position of the attenuator 529 placed in front of the illumination light source 513 is so controlled to change the transmittance of the attenuator that the illumination intensity is set P0. By setting P0 as above, it is possible to illuminate the sample 1 with the illumination intensity P0 set by the processing system 25.

Further, in FIG. 8A, an example of controlling the illumination intensity by changing the position of the attenuator 529 has been described. It is also possible to use an ND filter where the optical density continuously changes in place of the attenuator 529, to change the coordinates of the ND filter, so as to control the illumination intensity of the dark field illumination unit 501. Further, it is possible to control the illumination intensity to P0 by providing a polarizer in place of the attenuator 529 and rotating the polarizer provided on the optical axis of the above-described illumination light source 513 to obtain the illumination intensity set by the control system 25. Note that in the illumination intensity control method using the polarizer, as the polarization condition is changed by the set illumination intensity, to cancel the change of polarization, ½ wave plate may be provided on the illumination light axis. Further, a method of controlling the illumination intensity of the illumination light source 513 by controlling the application voltage of the illumination light source 513 to obtain the above-described illumination intensity set by the processing system 25 is also possible. Further, it may be arranged such that the illumination intensity is set using the defect size information in the output data 101 from the other inspecting apparatus 7 in place of luminance value.

Figure 10:
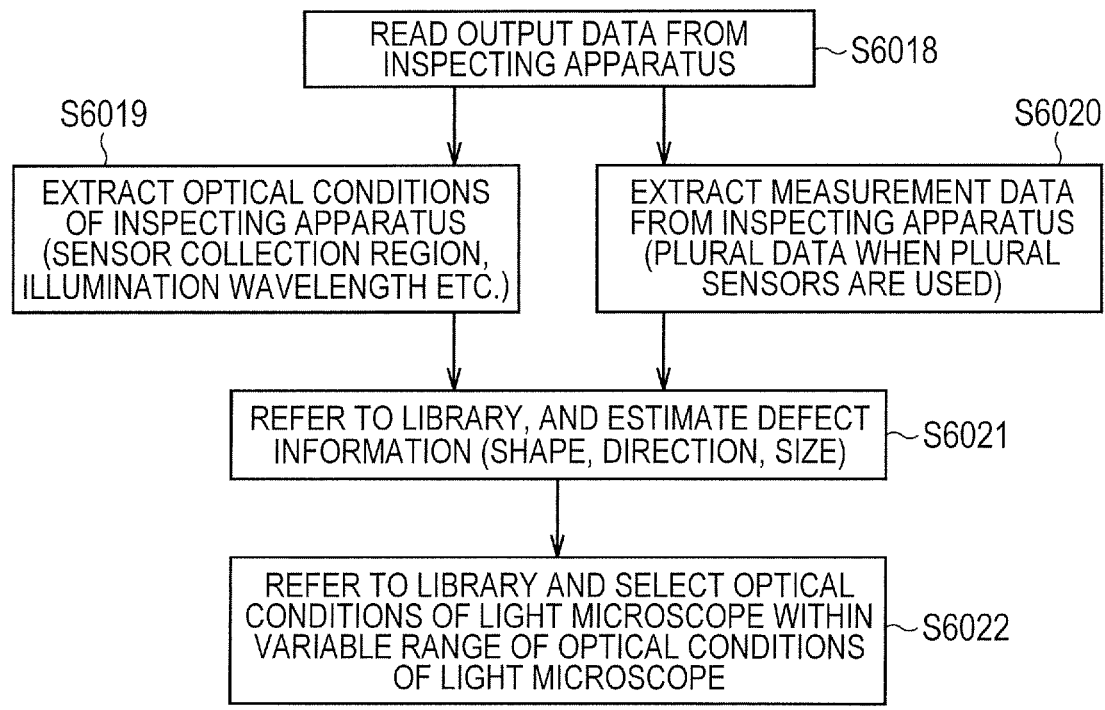
FIG. 10 is a flowchart showing the procedure of setting optical conditions in the optical microscope in the embodiment of the present invention.

A method of setting the detection conditions of the spatial distribution optical element will be described using FIG. 8B. The output data 101 including detection values of plural detectors 626 (for example, in a frame 398 in FIG. 10) capable of detecting scattered light at different azimuth angles, scattering angles, and the condition data 118 of the inspecting apparatus 7 including the optical conditions (illumination condition and detection condition) of the other defect inspecting apparatus 7 and the positional information of the detector are stored in the storage device 24 (S801). The output data 101 and the condition data 118 stored in the storage device 24 are read with the control system 25, and scattering intensity distribution tendency 120 of the detection object defect is obtained (S802).

Next, the scattering intensity distribution tendency 120 of the subject defect obtained by the control system 25 and the scattering intensity distribution tendency 112 of each defect shape stored in the library 22 are compared, and a defect shape 121 is estimated (S803). Appropriate optical condition data 119 by the defect shape stored in the library 22 is referred to, to select the spatial distribution optical element 201 capable of detecting the estimated defect shape 121 at high S/N (S804). At this time, it is necessary to select appropriate optical conditions in the configurable optical conditions of the optical microscope 5. To provide the selected spatial distribution optical element 210 on the optical axis 301 of the detection optical system, driving of the spatial distribution optical element holder 32 by controlling an unshown driving mechanism (S805). With this arrangement, it is possible to detect a defect at a high S/N with the spatial distribution optical element 201 corresponding to defect type.

Further, it may be arranged such that without estimating the defect shape, the control system 25 selects the spatial distribution optical element 201 to obtain high S/N from the scattering intensity distribution tendency of the inspection subject defect generated from the output information from the other defect inspecting apparatus 7. At this time, it is necessary to consider the difference between the inspecting optical conditions for the sample 1 in the other defect inspecting apparatus 7 and the configurable optical conditions in the optical microscope 5 or 5'. A method of previously storing in the library 22 the correction value for the optical conditions setting which causes due to the difference of optical conditions is conceivable. Further, when the spatial distribution optical element 201, capable of changing the optical properties is used by changing the application voltage applied to the spatial distribution optical element 201 instead of driving the spatial distribution optical element holder 32 with the driving mechanism, it is possible to set the spatial distribution optical element 201 corresponding to the defect by controlling the application voltage between electrodes so as to obtain the optical conditions selected with the control system 25. Further, as the optical conditions 119 set from the defect shape, not only the properties of the spatial distribution optical element 201 but also the illumination condition and the detection condition may be set.

Further, it is possible to control the illumination condition and the detection condition in correspondence with the set optical conditions. For example, when the optical microscope 5' capable of changing the illumination light incident direction described in FIG. 2B is used, it is possible to perform defect detection in correspondence with the direction of the defect based on the above-described defect shape estimated by the control system 25, by selecting an appropriate illumination direction and by rotating the swing mirror 526 to control the illumination direction by the control system 25. Thereby, it is possible to stabilize the detection sensitivity.

Further, the number of the detectors 626 of the other defect inspecting apparatus 7 is not necessarily plural. When a single detector 626 is used, a method of obtaining the scattering intensity distribution tendency using the output data 101 from the inspecting apparatus obtained on different optical conditions is conceivable. The different optical conditions are, for example, illumination direction and illumination wavelength, illumination intensity, polarization, spatial filter shape and the like. The scattering intensity distribution tendency 112 by the defect shape, previously stored in the library 22, and the appropriate optical conditions data 119 by defect shape are generated from the above-described scattered light simulation or experimental result.

Further, in the inspection of the sample 1 with the other defect inspecting apparatus 7, when the illumination light incident azimuth angle is not even on the sample 1, the output data 101 of the other defect inspecting apparatus 7 may include the illumination direction. At that time, by correcting defect coordinate based on the difference of the illumination direction of the measurement subject defect in the other defect inspecting apparatus 7 and deriving the estimated defect shape 121 from the corrected defect coordinate, it is possible to set more appropriate optical system.

Figure 9:
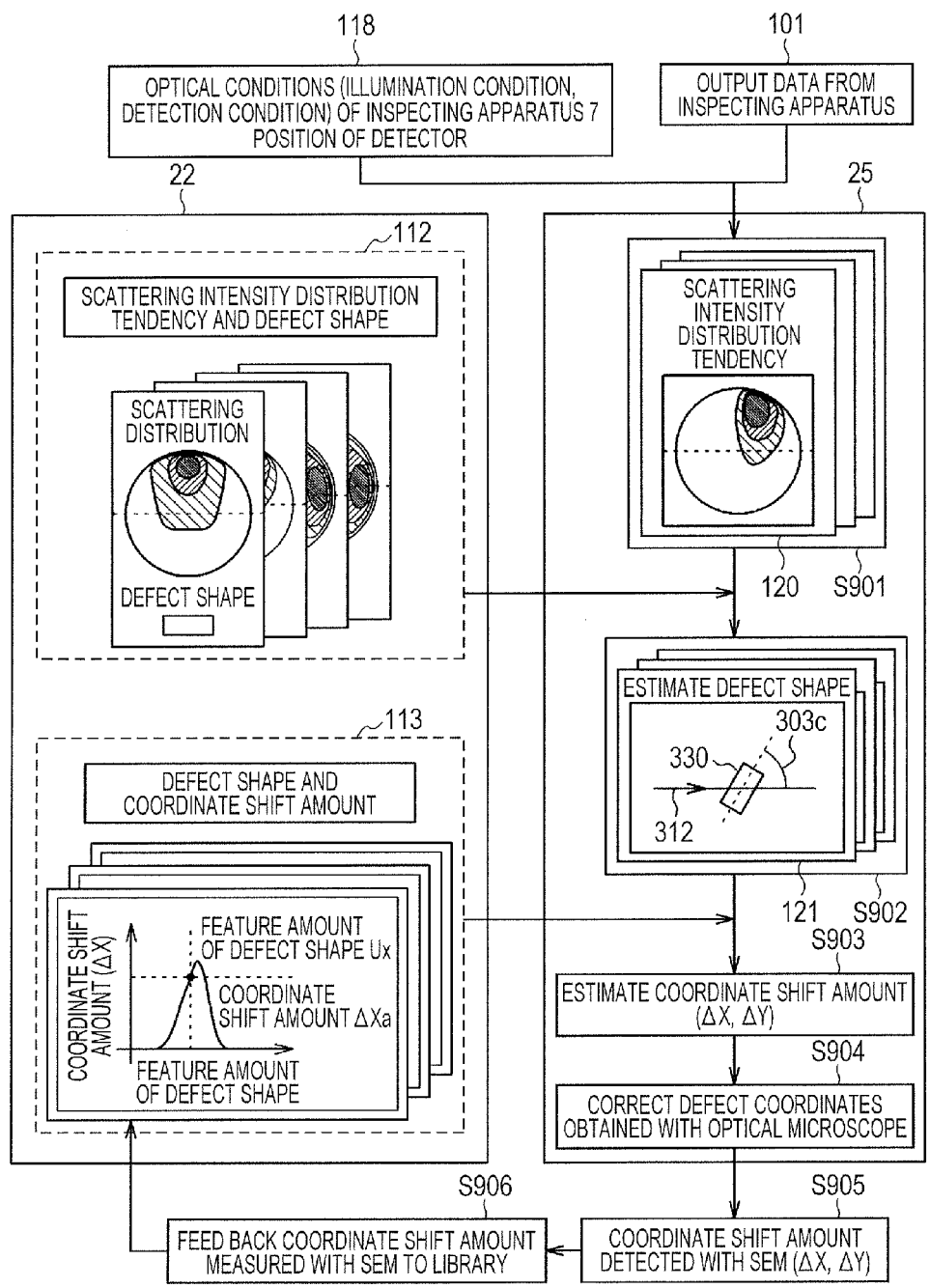
FIG. 9 is a flowchart showing the procedure upon defect observation in the embodiment of the present invention.

Next, an example of a method of correction amount calculation of the defect position with respect to each defect utilizing the data outputted from the other defect inspecting apparatus 7 will be described using FIG. 9. With respect to each defect detected by the other defect inspecting apparatus 7, the defect position correction amount to observe with the defect observing apparatus 100 is previously calculated and registered in the database 22. After the completion of the position correction amount calculation for plural defects or all the defects, observation is performed with the SEM 6. Upon previous calculation of defect position correction amount with respect to each defect, there is a method of deriving a coordinate shift amount (Δx, Δy) from the database 22, using the output data 101 from the inspecting apparatus 7, for example, information such as luminance of the defect or the size of luminescent spot, outputted from single or plural detectors of the inspecting apparatus 7, and performing coordinate correction. With this method, it is possible to perform coordinate correction in correspondence with shape or size of defect as an inspection subject, and it is possible to improve the coordinate correction accuracy.

Figure 8B:
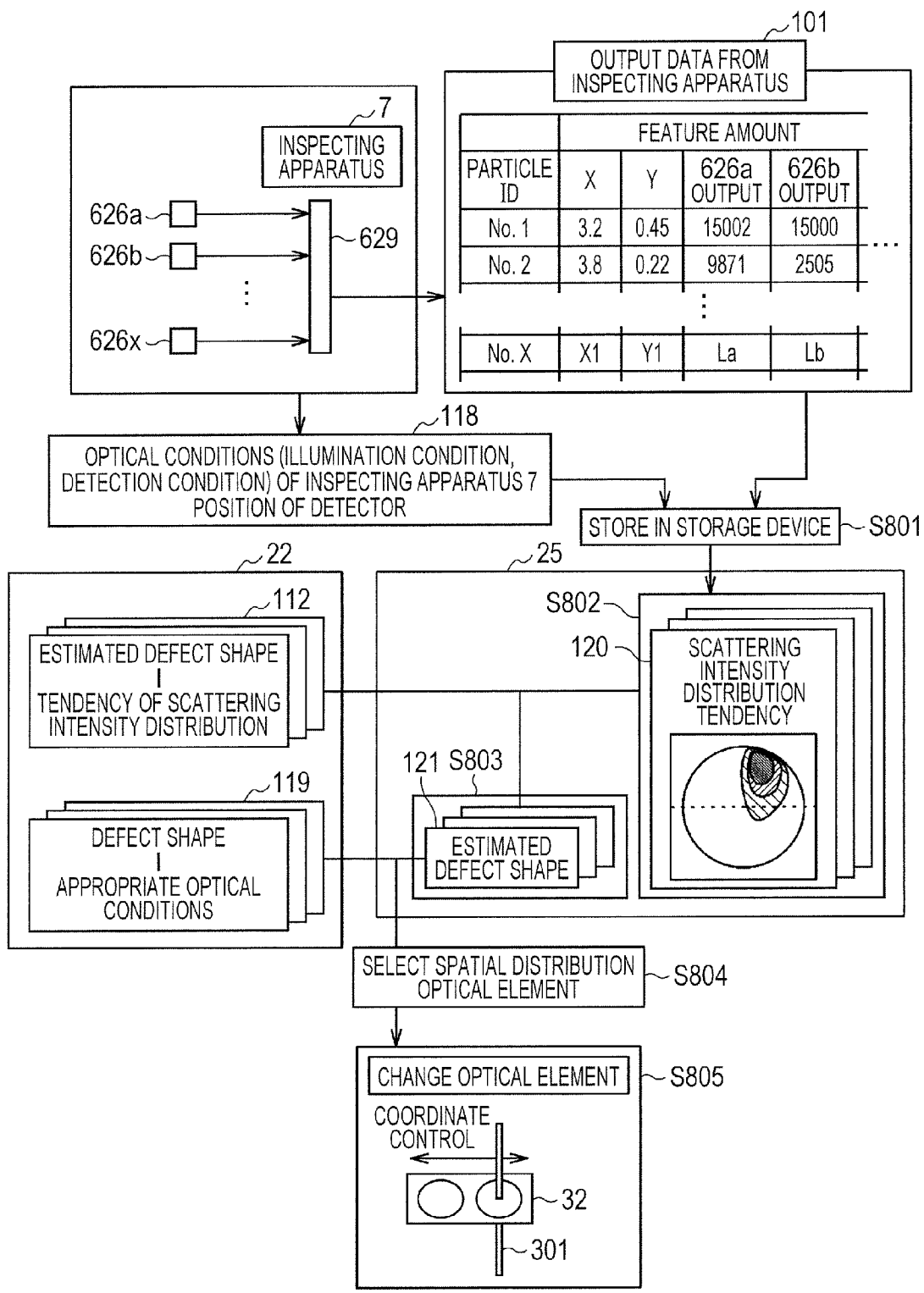
FIG. 8B is a block diagram showing the procedure of processing upon defect observation in the embodiment of the present invention.

In a similar procedure to the processing procedure described in FIG. 8B, the scattering intensity distribution tendency 120 as a detection subject is obtained with the control system 25 (S901), from the output data 101 including the defect coordinates, and the optical conditions (illumination condition and the detection condition) of the other defect inspecting apparatus 7, and the condition data 118 of the other defect inspecting apparatus 7 including the positional information of the detector. The obtained scattering intensity distribution shape 120 and the scattering intensity distribution information 112 by defect shape previously stored in the library 22 are referred to, and the inspection subject defect shape 121 is estimated (S902). Next, the coordinate shift amount 113 depending on defect shape stored in the library 22 is referred to, and the coordinate shift amount (Δx, Δy) 114 of the estimated defect shape 121 is derived (S903). The coordinates of the inspection subject defect, obtained by the optical microscope 5 are corrected (S904) using the derived coordinate shift amount (Δx, Δy). As the defect is observed with the SEM 6 using the corrected defect coordinates, it is possible to suppress the variation of the coordinate accuracy due to defect shape. Further, it is possible to improve the coordinate correction accuracy by calculating an actual coordinate shift amount from the detection result from the SEM 6 (S905) and feeding back it to the coordinate shift amount data 113 depending on defect shape stored in the library 22 (S906). The coordinate shift amount data 113 depending on defect shape previously stored in the library 22 is generated by simulation, experimental result, or actual data with the SEM.

Further, there is a method of performing the coordinate correction using not only the output data from the other defect inspecting apparatus 7 but also both the output data from the other defect inspecting apparatus 7 and the output data (defect coordinates and other than defect coordinates) from the optical microscope 5 or 5'. In this method, as the output data from the optical microscope 5 or 5', on the optical conditions different from the optical conditions (illumination condition and detection condition) of the other defect inspecting apparatus 7 can be used and the information amount is increased, it is possible to improve the coordinate correction accuracy.

Next, a method of using the output data from the other defect inspecting apparatus 7 will be described using FIG. 11. In some cases, the configurable optical conditions in the other inspecting apparatus 7 are different from those in the optical microscope 5 or 5'. Especially, there is a high probability that the sensor collecting region and the illumination light wavelength are different. In a case where the configurable optical conditions are different, when the optical conditions of the optical microscope 5 or 5' are set using the output data from the other defect inspecting apparatus 7, it is necessary to consider the influence due to the difference of the optical conditions with respect to the other defect inspecting apparatus 7. As a procedure, the output data from the other defect inspecting apparatus 7 is read from the storage device 24 (step S6018), the optical conditions of the other defect inspecting apparatus 7 are read from the read output data from the other defect inspecting apparatus 7 (step S6019). The optical conditions of the other defect inspecting apparatus 7 are, for example, the sensor collecting region (NA), illumination light wavelength, illumination light incident angle, illumination light polarization, detection polarization and the like. Next, measurement data is extracted from the output data from the other defect inspecting apparatus 7 (step S6020), then the library is referred to, then, from the measurement data of the other defect inspecting apparatus 7 extracted at step S6020 under the optical conditions of the other defect inspecting apparatus 7 extracted at step S6019, the defect information (shape, direction size and the like) is estimated (step S6021), and high sensitive optical conditions under the invariable optical conditions of the optical microscope 5 or 5' are selected (step S6022).

With this arrangement, it is possible to correct the influence due to the difference between the illumination light wavelength of the other defect inspecting apparatus 7 and the illumination light wavelength of the optical microscope 5 or 5' or the like. The library is previously generated by scattered light simulation or experimental result.

Next, a method of classifying defect type utilizing the difference of sensitivity of defect type by illumination light azimuth angle, estimation of defect shape, and estimation of defect direction will be described using FIG. 12. As shown in FIG. 6, the scattered light intensity distribution greatly differs in accordance with defect type, due to the difference of inclination of defect with respect to illumination light incident angle (defect direction). Using the dependency of defect direction on scattered light direction with respect to the illumination light incident angle, the defect type classification, the defect shape estimation and defect direction estimation are performed.

FIG. 6 shows that the defect type classification, the defect shape estimation and defect direction estimation are performed from the change of signal value from the defect while changing the illumination light azimuth angle 304. In a defect having isotropic scattering intensity distribution, even when the illumination direction is changed, the signal value from the defect has small change or no change. On the other hand, in a defect where the scattering intensity distribution differs by the difference of defect direction with respect to the illumination light incident angle as shown in FIG. 6, when the illumination direction is changed, the signal value from the defect is changed. Further, the change of the scattered light intensity distribution by change of defect direction differs in accordance with defect shape. Accordingly, it is possible to estimate the defect type, the defect shape and a defect direction (342) by changing the illumination direction to observe the defect, obtaining change 341 of the feature amount of the defect scattered light with respect to the illumination light azimuth angle, and by referring to the change 341 of the defect feature amount by the change of illumination direction from the database previously stored in the library 22.

Further, it is possible to perform the classification of defect type, estimation of defect shape and estimation of defect direction from the change of defect signal value by limiting the detection region or controlling the selection of the detection polarization by using the spatial filter or a polarization distribution optical element 201, and by changing the illumination direction. By using the spatial filter and the polarization distribution optical element 201, it is possible to perform higher accuracy estimation of defect type, defect shape and defect direction. For example, in a case where only frontward scattering light is transmitted using a spatial filter and the signal value from the defect is detected while the illumination direction is changed, when almost no direction dependency is found in the signal value, it is estimated that the subject defect is a spherical defect. When the region is extremely limited with the spatial filter, the scattered light from the defect is weak and may be submerged in noise.

Further, the change of illumination direction may not be discrete angular change but continuous angular change. Further, when detection is made from a discrete illumination direction, plural illumination directions may be selected based on the output result from the inspecting apparatus.

Further, it may be arranged such that the defect direction SEM optical conditions are set from the illumination direction dependency of the feature amount of scattered light from the defect obtained with the optical microscope 5. For example, to improve the SEM image sensing conditions, the sample is rotated or tilted (FIG. 3).

Further, it may be arranged such that the illumination light azimuth angle 304 of the optical microscope 5 is fixed, the spatial distribution optical element 201 is rotated in a horizontal plane with respect to the sample, plural result of observation of the sample 1 are obtained, the change of feature amount of the scattered light from the defect with respect to the rotation angle of the spatial distribution optical element 21 is obtained, and the estimation of defect type, defect shape and defect direction is performed from the obtained feature amount change of the scattered light.

As described above, the invention made by the present inventor has been particularly described based on the embodiment, however, the present invention is not limited to the above-described embodiment, and apparently various changes can be made within the range not departing from the subject matter.

REFERENCE SIGNS LIST

1 . . . sample 2 . . . sample holder 3 . . . stage 4 . . . optical height detecting system 5 . . . optical microscope 6 . . . electron microscope 7 . . . inspecting apparatus 11 . . . height control mechanism 12 . . . vacuum vessel 13 . . . vacuum sealing window 21 . . . network 22 . . . database 23 . . . user interface 24 . . . storage device 25 . . . control system 31 . . . optical element selecting mechanism 32 . . . spatial distribution optical element holder 301 . . . optical axis of detection optical system 302 . . . pupil plane 501 . . . dark field illumination unit 509 . . . solid-state image sensing device 510 . . . lens 511 . . . imaging lens 512 . . . condenser lens 513 . . . dark field illumination light source 514 . . . ND filter 515 . . . wave plate 516 . . . illumination lens group.

The invention claimed is:

1. A defect observing method comprising:
obtaining, by optical inspection with a first inspection apparatus, defect observation information of a defect on a sample, the defect observation information including first positional information, information on conditions of the optical inspection, and information on the result of inspection;
placing the sample on a table to observe the defect a second inspection apparatus and a SEM;
aligning the sample on the table using the second inspection apparatus and a bright field illumination light source;
setting initial detection conditions to optically detect the defect based on the defect observation information by including selecting a filter among a plurality of filters for the second inspection apparatus, wherein the filter has a function of transmitting and controlling scattered light on optical conditions such that a ratio of the scattered light from the substrate surface to the scattered light from the defect is adjusted based on a signal-to-noise ratio;
detecting, by optical inspection with the second inspection apparatus, the defect and obtaining a second positional information of the defect on the table;
correcting the first positional information based on the second positional information; and
observing the defect on the sample placed on the table with the SEM using the corrected positional information of the defect.

2. The defect observing method according to claim 1, wherein the obtained information on the conditions of the optical inspection by the first inspecting apparatus includes information on an azimuth angle of illumination light to illuminate the sample.

3. The defect observing method according to claim 1, wherein the obtained information on the conditions of the optical inspection with the first inspecting apparatus is information on optical inspection conditions by dark field illumination and information on the result of optical inspection by the first inspecting apparatus.

4. The defect observing method according to claim 1, wherein the obtained information on the conditions of the optical inspection with the first inspecting apparatus includes information on an optical element used in an optical system to detect scattered light from the sample and information on the result of optical inspection with the first inspecting apparatus.

5. The defect observing method according to claim 1, wherein at the step of setting initial detection conditions to optically detect the defect, a plurality of optically different inspection conditions are set, and wherein at the step of obtaining observation information, classification of the extracted defect is performed further using inspection information in the set plurality of optically different inspection conditions.

6. A defect observing method comprising the steps of:
obtaining, by optical inspection with a first inspection apparatus, defect observation information of a defect on a sample, the defect observation information including first positional information of a defect, information on conditions of the optical inspection, and information on the result of inspection;
placing the sample on a table to observe the defect with a second inspection apparatus and a SEM;
aligning the sample on the table using the second inspection apparatus and a bright field illumination light source;
setting initial detection conditions to optically detect the defect based on the defect observation information by including selecting a filter among a plurality of filters for the second inspection apparatus, wherein the filter has a function of transmitting and controlling scattered light on optical conditions such that a ratio of the scattered light from the substrate surface to the scattered light from the defect is adjusted based on a signal-to-noise ratio, detecting, by optical inspection with the second inspection apparatus, the defect based on the set initial detection condition, and obtaining the second positional information of the defect on the table;

correcting the first positional information of the defect detected by inspection with the first inspecting apparatus based on a second positional information; and observing the defect on the sample placed on the table with the SEM using the corrected positional information of the defect.

7. The defect observing method according to claim 6, wherein the obtained information on the optical inspection with the first inspecting apparatus includes information on an azimuth angle of illumination light to illuminate the sample.

8. The defect observing method according to claim 6, wherein the obtained information on the conditions of the optical inspection with the first inspecting apparatus is information on the optical inspection conditions by dark field illumination and information on the result of optical inspection with the first inspecting apparatus.

9. The defect observing method according to claim 6, wherein the obtained information on the optical inspection with the first inspecting apparatus includes information on an optical element used in an optical system to detect scattered light from the sample and information on the result of optical inspection with the first inspecting apparatus.

10. The defect observing method according to claim 6, wherein at the step of setting initial detection conditions to optically detect the defect, a plurality of optically different inspection conditions are set, and wherein at the step of obtaining observation information, classification of the extracted defects is performed further using inspection information in the set plurality of optically different inspection conditions.

11. A defect observing apparatus comprising:

table means movable while holding a sample;

SEM means for observing the sample placed on the table means;

optical microscope means for detecting a defect on the sample placed on the table means;

defect information storage means for storing observational information of a defect on a sample detected by optical inspection with a first inspecting apparatus, the defect observation information including first positional information on the optical inspection, and inspection result information; and control means for controlling the table, the SEM and the optical microscope, wherein the control means:

aligns the sample on the table using the optical microscope means and a bright field illumination light source, sets initial detection conditions to optically detect the defect based on the defect observation information;

detects the defect using the optical microscope means under the set initial detection condition by controlling the optical microscope means, wherein controlling the optical microscope means includes selecting a filter among a plurality of filters for the second inspection apparatus, wherein the filter has a function of transmitting and controlling scattered light on optical conditions such that a ratio of the scattered light from the substrate surface to the scattered light from the defect is adjusted based on a signal-to-noise ratio;

obtains a second positional information of the defect on the table means, corrects the first positional information based on the second positional information, controls the table means based on the corrected positional information, performs image sensing on the defect using the SEM means, and obtains the defect image.

12. The defect observing apparatus according to claim 11, wherein the control means extracts a defect detected by the optical microscope means with the set detection condition from defects detected by the first inspecting apparatus, and corrects the first positional information of the defect detected by the first inspecting apparatus stored in the defect information storage means based on the second positional information of the extracted defect on the table means obtained by detecting the extracted defect by the optical microscope means.

13. The defect observing apparatus according to claim 11, wherein the defect information storage means holds information including information on an azimuth angle of illumination light to illuminate the sample as the information on the conditions of the optical inspection with first inspecting apparatus.

14. The defect observing apparatus according to claim 11, wherein the optical microscope means has a dark field illumination optical system and a bright field illumination optical system, and wherein the defect information storage means holds information including the conditions of the optical inspection of the dark field illumination optical system of the optical microscope means as the information on the conditions of the optical inspection with the first inspecting apparatus.

15. The defect observing apparatus according to claim 11, wherein the optical microscope means has an optical system to detect scattered light from the sample via the optical element, and wherein the defect information storage means includes information on the optical element of the optical system to detect the scattered light by the optical microscope means and information on the result of optical inspection with the first inspecting apparatus, as the information on conditions of the optical inspection with the first inspecting apparatus.

16. The defect observing apparatus according to claim 11, wherein the optical microscope means has a function of performing inspection under a plurality of optically different inspection conditions, and has a function of classifying the defects from inspection information under the plurality of inspection conditions.

* * * * *